US011110399B2

United States Patent
Zavrel et al.

(10) Patent No.: US 11,110,399 B2
(45) Date of Patent: Sep. 7, 2021

(54) PROCESS FOR THE PURIFICATION OF BIOMASS HYDROLYSATE

(71) Applicant: Clariant International Ltd., Muttenz (CH)

(72) Inventors: Michael Zavrel, Olching (DE); Danielle Dennewald, Munich (DE); Philip Hoffmann, Munich (DE)

(73) Assignee: Clariant International Ltd., Muttenz (CH)

( * ) Notice: Subject to any disclaimer, the term of this patent is extended or adjusted under 35 U.S.C. 154(b) by 557 days.

(21) Appl. No.: 15/758,724

(22) PCT Filed: Aug. 19, 2016

(86) PCT No.: PCT/EP2016/069740
§ 371 (c)(1),
(2) Date: Mar. 8, 2018

(87) PCT Pub. No.: WO2017/042019
PCT Pub. Date: Mar. 16, 2017

(65) Prior Publication Data
US 2018/0304200 A1    Oct. 25, 2018

(30) Foreign Application Priority Data

Sep. 11, 2015   (EP) .................................... 15184893

(51) Int. Cl.
*B01D 61/44*     (2006.01)
*B01D 61/42*     (2006.01)
(Continued)

(52) U.S. Cl.
CPC ......... *B01D 61/422* (2013.01); *B01D 15/361* (2013.01); *B01J 20/103* (2013.01);
(Continued)

(58) Field of Classification Search
CPC .... B01D 61/422; B01D 15/361; B01D 15/00; C08H 8/00; C13K 1/04; B01J 20/103;
(Continued)

(56) References Cited

U.S. PATENT DOCUMENTS 7,819,976 B2 * 10/2010 Friend ..................... C13K 1/02
127/1
2010/0159521 A1   6/2010 Cirakovic et al.
2013/0295629 A1   11/2013 Weider et al.

FOREIGN PATENT DOCUMENTS

JP          2005229821 A      9/2005

OTHER PUBLICATIONS

Bradford, M.M., "A Rapid and Sensitive Method for the Quantitation of Microgram Quantities of Protein Utilizing the Principle of Protein-Dye Binding", Analytical Biochemistry, vol. 72, 1976, pp. 248-254.
(Continued)

*Primary Examiner* — Arun S Phasge
(74) *Attorney, Agent, or Firm* — Verrill Dana, LLP

(57) ABSTRACT

The present invention is directed to a novel and advantageous process for the purification of biomass hydrolysate as well as the purified hydrolysate produced after the inventive process and the use of the purified hydrolysate as a fermentation medium.

15 Claims, 9 Drawing Sheets

(51) Int. Cl.
  *C08H 8/00* (2010.01)
  *C13K 1/04* (2006.01)
  *B01D 15/36* (2006.01)
  *B01J 20/10* (2006.01)
  *B01J 20/12* (2006.01)
  *B01J 20/20* (2006.01)
  *B01D 15/00* (2006.01)
  *C12P 7/44* (2006.01)
  *C12N 9/24* (2006.01)
  *C12P 19/04* (2006.01)

(52) U.S. Cl.
  CPC ............... *B01J 20/12* (2013.01); *B01J 20/20* (2013.01); *C08H 8/00* (2013.01); *C13K 1/04* (2013.01); *B01D 15/00* (2013.01); *C12N 9/2402* (2013.01); *C12P 7/44* (2013.01); *C12P 19/04* (2013.01)

(58) Field of Classification Search
  CPC ... B01J 20/12; B01J 20/20; C12P 7/44; C12P 19/04; C12N 9/2402
  See application file for complete search history.

(56) References Cited

OTHER PUBLICATIONS

V. Menon, et al., "Trends in bioconversion of lignocellulose: Biofuels, platform chemicals & biorefinery concept", Progress in Energy and Combustion Science, 38, Feb. 14, 2012, pp. 522-550.
Wu, Wutong ed., "Chapter VI. Adsorption separation method", Biopharmaceutical Technology 2018, published by China Medical Science Press, English translation of pp. 159-160 and 162-168.

\* cited by examiner

PROCESS FOR THE PURIFICATION OF BIOMASS HYDROLYSATE

The present invention is directed to a novel and advantageous process for the purification of biomass hydrolysate as well as the purified hydrolysate produced by the inventive process and the use of the purified hydrolysate as a fermentation medium.

Lignocellulosic biomass originating from agricultural residues such as sugar cane bagasse, wheat straw, barley straw and other saccharide- or polysaccharide- and protein-containing material are valuable sources not only for refined saccharides such as monomeric or dimeric sugars, but also for other components such as amino acids, proteins and minerals.

There are various processes within the state of the art for separating components such as particularly sugars from sugar beets and sugar cane. Solutions resulting from the treatment of these so-called "first generation" substrates are usually relatively pure sugar solutions and they can be used as they are in standard processes without major impact on the process efficiency. In contrast, solutions resulting from the hydrolysis of "second generation" substrates based on agricultural residues such as sugar cane bagasse, wheat straw or barley straw are complex mixtures of proteins, minerals and sugars. They also include organic acids, colored particles, degradation products from lignin and other impurities. This makes these second generation hydrolysates unsuitable for further processing such as the preparation of poly lactic acid from lactic acid. Existing processes involving this type of hydrolysates also suffer from severe fouling in tubes, pipes, on membranes and in other process units applied, reducing the efficiency of the process, making more frequent cleaning and replacement of process units necessary leading to significantly higher costs.

Thus, there is a need for a process enabling the preparation of a highly purified hydrolysate of biomass containing a maximum amount of valuable compounds such as monomeric and dimeric sugars, but only a minimum amount of impurities. Such a process increases the possibilities of further processing and possible applications of the hydrolysate.

It is the object underlying the present invention to provide a process for the purification of biomass hydrolysate to prepare a hydrolysate which does not show the disadvantages of the processes known within the state of the art.

In a first aspect, the invention thus provides a process for the purification of biomass hydrolysate comprising the steps
a) Providing a biomass hydrolysate;
b) Adjusting the temperature of the biomass hydrolysate to a temperature selected from the range of from 50 to 95° C.;
c) Addition of at least one acid to the biomass hydrolysate;
d) Solid-liquid separation of the biomass hydrolysate-acid mixture to obtain a solid phase and a liquid phase;
e) Deionization of the liquid phase of the hydrolysate-acid mixture after separation according to step d).

It has surprisingly been found by the inventors of the present invention that the combination of an adjustment of temperature and the addition of an acid—which will even increase the ion content of the solution—will lead to an improvement of a later deionization and thereby to an improved purified hydrolysate. The deionization is improved in two aspects: the quantity of salts removed during the deionization is increased and the fouling in the deionization unit and surrounding parts of the process is reduced. A further advantage of the present invention is that the process can also be applied if the biomass hydrolysate contains organic acids.

The term "biomass" as used within the present invention refers to any type of biomass known to a person skilled in the art as suitable for the inventive process. Particularly preferred is biomass of plant-origin. Within a further preferred embodiment, the initial dry matter content of the biomass is selected from 10 to 100 wt.-%, more preferred from 35 to 95 wt.-% and particularly preferred from 40 to 80 wt.-%. The term "dry matter" (d.m.) refers to the mass to biomass ratio determined after water and other volatile compounds have been removed from fresh tissue using an IR-balance. It is thereby particularly preferred to select a biomass whereby its dry matter contains at least 25 wt.-% of saccharides such as monomeric sugars, dimeric sugars and oligosaccharides and/or polysaccharides, more preferred at least 40 wt.-%, particularly preferred at least 60 wt.-%, further preferred at least 80 wt.-% of saccharides such as monomeric sugars, dimeric sugars and oligosaccharides and/or polysaccharides. Further, any mixtures of suitable biomasses are to be included within the term "biomass".

Particularly preferred biomass is "lignocellulose biomass".

The term "lignocellulose biomass" refers to residue-, waste- and/or by-products from forestry and agriculture, the food-processing and paper industry and communal waste. In particular, the term "lignocellulose biomass" as used within the present invention includes grain straw and/or spelt (such as wheat, rye, barley, oats), maize straw, stover and/or spindles, grasses such as Sericea lespedeza, switchgrass (Panicum virgatum), Napier grass (Miscanthus; China reed), Sudan grass (Sorghum sudananse, Sorghum drummondi), Arundo donax, barks, wood, wood residues, wood chips and/or wood chippings, fruit pulp, rice straw, banana leaves, empty fruit bunches and agave residues.

Further biomass suitable for the process are manure from stables, herbaceous materials, coffee grinds and waste from oil mills such as rapeseed pressed cake and sewage from mills, paper-making stock and waste water from paper mills, waste paper, vegetable and fruit leftovers.

Within a preferred embodiment of the process of the present invention, the biomass is selected from cellulose, hemicellulose and/or lignin-containing biomass.

Within a particularly preferred embodiment of the process of the present invention the biomass is selected from sugar beet pulp, sugar cane bagasse, sugar cane straw, wheat straw, wood and mixtures thereof.

Within another particularly preferred embodiment of the process of the present invention the biomass is lignocellulosic biomass from agricultural residues, such as wheat straw, barley straw, soy bean straw, sugar cane bagasse, sugar cane leaves and stalks, sugar cane straw, maize straw, barley straw, stover and mixtures thereof.

The term "biomass hydrolysate" as used within the present invention is to be understood as depicting a depolymerized polymer which was depolymerized by a hydrolysis reaction. "Hydrolysis reaction" is to be understood as the cleavage of chemical bonds by the addition of water. One way to perform hydrolysis technically is to add hydrolase enzymes to the biomass.

Within a preferred embodiment, the biomass hydrolysate comprises at least 50 wt.-% saccharides in the form of monomeric and dimeric sugars, preferably at least 65 wt.-%, more preferred at least 75 wt.-%, also preferred at least 85 wt.-% and most preferred 99 wt.-% all relative to the dry matter (d.m.) of the biomass. Within a further preferred embodiment, the biomass hydrolysate comprises amino acids, oligopeptides, minerals, oligosaccharides and/or proteins as well as organic acids. The content in minerals is preferably at least 0.5 wt.-% salts, preferably at least 1 wt.-%, more preferred at least 2 wt.-% and most preferred 3 wt.-% all relative to the dry matter (d.m.) of the biomass. The biomass hydrolysate may comprise organic acids such as formic acid, acetic acid, galacturonic acid and lactic acid. It may also comprise the following degradation products: phenolic compounds such as 4-hydroxy-3-methoxyphenyl and 4-hydroxy-3,5-dimethoxyphenyl, ferulic acid, 4-hydroxybenzoic acid, levulinic acid, furfurals, 5-hydroxymethylfurfural, tannins and terpenes.

The biomass hydrolysate as used within the process of the present invention has preferably been prepared according to the following methods:

It is preferred to provide the biomass in particulate form e.g. by cutting, milling, grinding, shearing, shear-dispersing, chopping, dispersing and/or blending the biomass prior to step (a). Within a further embodiment, the biomass might be subjected to a pre-treatment process.

Methods suitable for the pretreatment of the biomass include any kind of mechanical, biological, chemical and/or physical pretreatment methods known to a person skilled in the art. Within a preferred embodiment, the pretreatment method is selected from the methods of mechanical comminution, treatment with acids and/or alkalines, wet oxidation, pH-controlled hydrothermolysis and/or steam explosion.

"Steam explosion" preferably comprises a pressurized hydrothermal treatment at a temperature of from 60 to 350° C., preferably from 80 to 300° C., particularly preferred from 100 to 250° C. and most preferred from 110 to 220° C. of the lignocellulose-containing material in the absence or presence of acid (such as $H_2SO_4$, HCl, $H_3PO_4$) or base/alkaline (i.e. $NH_4OH$, NaOH, KOH, lime) catalysts, which are—if present—added at concentrations from 0.01 to 15% (wt./wt.), preferably from 0.05 to 12.5% (wt./wt.), more preferred from 0.1 to 10% (wt./wt.) and most preferred from 0.25 to 7.5%. In a preferred embodiment the pressure is preferably selected from 1 to 100 bar, preferably from 2 to 50 bar, also preferred from 3 to 25 bar and most preferred from 5 to 15 bar. Reaction times during steam explosion have to be selected from 10 s to 2 h, preferably from 1 minute to 1.5 hours, and most preferred from 5 minutes to 1 hour to provide for efficient transformation of the biomass components in preparation for enzymatic hydrolysis. Within a particularly preferred embodiment a "mechanical comminution" pretreatment of the lignocellulose-containing material is carried out before or during the steam explosion pretreatment, wherein the mechanical comminution is selected from the group consisting of mechanical processing, grinding, chopping, crushing, cutting, irradiation, milling and combinations thereof.

"Acid pretreatment" preferably constitutes a continuous dilute and/or mild acid treatment, such as, treatment with sulfuric acid, or another organic acid, such as acetic acid, formic acid, lactic acid, phosphoric acid, nitric acid, citric acid, tartaric acid, succinic acid, hydrogen chloride or mixtures thereof. Other acids may also be used. A "mild acid treatment" is to be understood as carried out at a pH of from 0.1 to 5, preferably pH from 2 to 3. In a preferred embodiment the acid is added in concentrations from 0.01 to 15wt.-% (wt./wt.), preferably from 0.05 to 12.5wt.-% (wt./wt.), more preferred from 0.1 to 10wt.-% (wt./wt.) and most preferred from 0.25 to 7.5wt.-%. The acid is preferably sulfuric acid. The acid may be contacted with the biomass at a temperature in the range of from 120 to 280° C., preferably from 135 to 225° C. and most preferred from 150 to 200° C. for a period from 1 to 60 minutes, preferably 2 to 30 minutes and most preferred from 5 to 15 minutes. Addition of strong acids, such as sulphuric acid, may be applied within particularly preferred embodiments to remove hemicellulose.

"Chemical pretreatment" also pertains to treatment of the biomass with $H_2O_2$, ozone, Lewis acids, $FeCl_3$, $Al_2(SO_4)_3$ in aqueous alcohols, glycerol, dioxane, phenol, ethylene glycol, NaOH, $Na_2CO_3$ and/or ammonia. Preferred concentrations, temperature and duration are chosen analogous to the conditions referenced above regarding acid pretreatment.

"Wet oxidation pretreatment" involves the use of oxidizing agents, such as sulphite based oxidizing agents.

The term "mechanical comminution" refers to any mechanical treatment which promotes the separation and/or release of cellulose, hemicellulose and/or lignin from the biomass.

Mechanical comminution is preferably selected from the group consisting of mechanical processing, grinding, chopping, crushing, cutting, irradiation, milling such as dry milling, wet milling and vibratory ball milling, and combinations thereof.

"Biological pretreatment" refers to any biological pretreatment which promotes the separation and/or release of cellulose, hemicellulose, and/or lignin from the biomass. Biological pretreatment techniques can involve applying lignin-solubilizing microorganisms such as actinomycetes (e.g. *Streptomyces* strains) or white rod fungi.

Pretreatment methods as described before are to be carried out within suitable devices known to a person skilled in the art. A device suitable for carrying out chemical pretreatment may be any kind of vessel such as a tank reactor or a stirred tank reactor. A device suitable for carrying out steam explosion may be any kind of vessel such as a tank reactor or a stirred tank reactor but may also be carried out within a screw reactor, preferably a continuous screw reactor, or within a plug flow reactor, preferably a continuous plug flow reactor.

The dry matter content of pretreated biomass is preferably selected from 20 to 60 wt.-%, particularly preferred from 35 to 50 wt.-%, wherein it is most preferred that the biomass has been pretreated by a method not involving the addition of any acid and/or alkalines.

It is, however, a particular advantage of the process for the hydrolysis of biomass that also the application of relatively large and/or un-pretreated biomass particles will still achieve favorable results. The size of the biomass particles is preferably such that at least 90 wt.-% of the particles have a maximum length of 200 mm, more preferred 100 mm, even more preferred 50 mm and most preferred 25. It is further preferred that the size of the biomass particles is preferably such that at least 95 wt.-% of the particles have a maximum length of 200 mm, more preferred of 100 mm, even more preferred of 50 mm and most preferred of 25 mm.

The pretreated biomass is then preferably contacted with an enzyme-composition containing at least one enzyme selected from the class of hydrolases.

The term "contacting" (or "contacted") comprises any kind of contacting of biomass with an enzyme composition known to a person skilled in the art as suitable for the inventive process. Within a preferred embodiment, the "contacting" of the biomass with the enzyme composition is carried out by adding the enzyme composition to the biomass. Further, it is particularly preferred that the addition of the enzyme composition is followed by or carried out concurrently with a mixing of the enzyme composition and the biomass.

The term "enzyme composition" refers to any composition comprising at least one enzyme selected from the class of hydrolases. The at least one enzyme selected from the class of hydrolases amounts preferably to from 1 to 99.99 wt.-% (relative to the weight of the enzyme composition), further preferred to from 5 to 99 wt.-%, particularly preferred to from 10 to 95 wt.-% and most preferred to from 20 to 90 wt.-% and may further contain at least one enzyme selected from the class of lyases. Within embodiments, wherein the enzyme-composition contains at least one enzyme selected from the class of lyases, the at least one enzyme selected from the class of hydrolases preferably amounts to from 0.01 to 50 wt.-% (relative to the weight of the enzyme composition), preferred to from 0.05 to 20 wt.-%, more preferred to from 0.08 to 5 wt.-% and most preferred to from 0.1 to 1 wt.-%.

Within a preferred embodiment, the enzyme composition contains cellulases, hemicellulases and/or pectinases.

Within a particularly preferred embodiment the enzyme composition contains at least one cellobiohydrolase (EC 3.2.1.–) and at least one endo-,4-β-glucanase (EC 3.2.1.4).

Within a particularly preferred embodiment, the enzyme composition contains at least one cellobiohydrolase (EC 3.2.1.–), at least one endo-,4-β-glucanase (EC 3.2.1.4), at least one β-glucosidase (EC 3.2.1.4), at least one glycoside hydrolase 61 (GH61 and CBM33), at least one endo-xylanases (EC 3.2.1.8) and at least one β-xylosidases (EC 3.2.1.37).

Within a particularly preferred embodiment the above defined enzyme composition further contains one or more enzymes selected from β-glucanase (EC 3.2.1.–), acetylxylan esterase (EC 3.1.1.72), acetylgalactan esterase (3.1.1.6)), α-arabinopyranosidase (3.2.1.–), α-galactosidase (EC 3.2.1.22), β-galactosidase (EC 3.2.1.23), α-glucuronidases (EC 3.2.1.139), β-mannase (EC 3.2.1.78), pectin methyl esterase (EC 3.1.1.11), pectin acetyl esterase (EC 3.1.1.–), rhamnogalacturonase (EC 3.2.1.–; GH28), rhamnogalacturonan acetylesterase (EC 3.1.1.86), rhamnogalacturonan endolyase (EC 4.2.2.23), rhamnogalacturonan lyase (EC 4.2.2.–) and β-mannosidases (EC 3.2.1.25), polygalacturonases (EC 3.2.1.15, 67, 82; GH28) and pectin/pectate lyases (EC 4.2.2.2, 6, 9, 10).

The terms "cellulases", "hemicellulases" and "pectinases" refer to any blend of enzymes which is involved in the hydrolytic degradation (depolymerization) of polymeric cellulose, hemicellulose and/or pectin to monomeric sugars. As used herein, the terms "cellulases", "hemicellulases" and "pectinases" refer to both naturally occurring and non-naturally occurring blends that include a plurality of enzymes as produced by an organism, for example a filamentous fungus. "Cellulases", "hemicellulases" and "pectinases" are preferably derived from fungi such as members of the subdivision Eumycota and Oomycota, including but are not limited to the following genera: *Aspergillus, Acremonium, Aureobasidium, Beauveria, Cephalosporium, Ceriporiopsis, Chaetomium, Chrysosporium, Claviceps, Cochiobolus, Cryptococcus, Cyathus, Endothia, Endothia mucor, Fusarium, Gilocladium, Humicola, Magnaporthe, Myceliophthora, Myrothecium, Mucor, Neurospora, Phanerochaete, Podospora, Paecilomyces, Pyricularia, Rhizomucor, Rhizopus, Schizophylum, Stagonospora, Talaromyces, Trichoderma, Thermomyces, Thermoascus, Thielavia, Tolypocladium, Trichophyton,* and *Trametes.* In a preferred implementation, the filamentous fungus is a *Trichoderma* species.

Within a preferred embodiment of the enzyme-composition the cellulases and/or pectinases are from a fungal source. Within a particularly preferred embodiment of the enzyme-composition, this fungal source is *Trichoderma reesei.*

The term "blend of enzymes" preferably refers to a blend of enzymes secreted from one single or more microbial sources. In some embodiments, enzymes for use in these blend(s) of enzymes can be prepared from one or more naturally occurring or engineered strains of filamentous fungi. Preferred strains are listed above. The desired ratio of enzyme components within the final blend(s) can be achieved by altering the relative amount of enzyme in the final blend e.g. by supplementation of purified or partially purified enzyme(s). In some embodiments, the final blend(s) may be supplemented with one or more enzyme activities that are not expressed endogenously, or expressed at relatively low level by the filamentous fungi, to improve the degradation of the cellulosic substrate to fermentable sugars. The supplemental enzyme(s) can be added as a supplement to the final blend(s) and the enzymes may be a component of a separate whole fermentation broth, or may be purified, or minimally recovered and/or purified.

The term "cellulase" refers to any enzyme capable of hydrolyzing cellulose polymers to shorter oligomers and/or glucose. Cellulases preferred within the enzyme composition include cellobiohydrolases (CBH) (EC 3.2.1.–), endo-1,4-β-glucanases (EG) (EC 3.2.1.4)), β-glucosidase (EC 3.2.1.4), cellobiose hydrolase (EC 3.2.1.21), glycoside hydrolase 61 (GH61 and CBM33), expansin, swollenin, loosinin and CIP Proteins (EC 3.1.1.–; CE15).

The term "hemicellulase" refers to any enzyme capable of degrading or supporting the degradation of hemicellulose. Hemicellulases preferred within the enzyme composition include β-glucanases (EC 3.2.1.–), endo-xylanases (EC 3.2.1.8), β-xylosidases (EC 3.2.1.37), acetylxylan esterase (EC 3.1.1.72), acetylgalactan esterase (3.1.1.6), acetyl mannan esterase, feruloyl esterase (EC 3.1.1.73), glucuronoyl esterase (EC 3.1.1.–), α-L-arabinofuranosidase (EC 3.2.1.55), α-arabinopyranosidase (3.2.1.–), α-galactosidase (EC 3.2.1.22), β-galactosidase (EC 3.2.1.23), α-glucuronidases (EC 3.2.1.139), β-mannase (EC 3.2.1.78), β-mannosidases (EC 3.2.1.25), mannan 1,4-mannobiosidase (EC 3.2.1.100), arabinogalactan endo-beta-1,4-galactanase (EC 3.2.1.89), endo-beta-1,3-galactanase (EC 3.2.1.90), galactan endo-beta-1,3-galactanase (EC 3.2.1.181, glucuronoarabinoxylan endo-1,4-beta-xylanase (EC 3.2.1.136), alpha-L-fucosidase (EC 3.2.1.51), coniferin beta-glucosidase (EC 3.2.1.126), xyloglucan hydrolases (EC 3.2.1.150, 151, 155), xylan α-1,2-glucuronosidase (EC 3.2.1.131), endo-xylogalacturonan hydrolase (EC 3.2.1.–; GH28), α-amylase (EC 3.2.1.1), glucan 1,4-α-glucosidase (EC 3.2.1.3), galactan 1,3-galactosidase (GH43), -1,4,-endogalactanase (EC 3.5.1.89; GH53), α-rhamnosidase (EC 3.2.1.40), β-rhamnosidase (EC 3.2.1.43), lignin peroxidase (EC 1.11.1.14), Mn peroxidase (EC 1.11.1.13), aryl-alcohol oxidase (EC 1.1.3.7), glyoxal oxidase (EC 1.1.3.), carbohydrate oxidases (EC 1.1.3.4, 9, 10), laccase (EC 1.10.3.2) and cellobiose dehydrogenase (EC 1.1.99.18).

The term "pectinase" refers to any enzyme capable of degrading or supporting the degradation of pectin. Pectinases preferred within the enzyme composition include polygalacturonases (EC 3.2.1.15, 67, 82; GH28), pectin/pectate lyases (EC 4.2.2.2, 6, 9, 10), pectin methyl esterase (EC 3.1.1.11), pectin acetyl esterase (EC 3.1.1.-), rhamnogalacturonase (EC 3.2.1.-; GH28), rhamnogalacturonan acetylesterase (EC 3.1.1.86), rhamnogalacturonan endo-lyase (EC 4.2.2.23), rhamnogalacturonan lyase (EC 4.2.2.-), rhamnogalacturonan galacturonohydrolase (EC 3.2.1.-), xylogalacturonan hydrolase (EC 3.2.1.-), pectin methylesterase (EC 3.1.1.11), beta-arabinofuranosidase (EC 3.2.1.55), beta-1,4-galactanase (EC 3.2.1.89), beta-1,3-galactanase (EC 3.2.1.90), beta-galactosidase (EC 3.2.1.23), alpha-galactosidase (EC 3.2.1.22), feruloyl acetyl esterase (EC 3.1.1.-), alpha-fucosidase (EC 3.2.1.51), (beta-fucosidase) (EC 3.2.1.38), beta-apiosidase (EC 3.2.1.-), alpha-rhamnosidase (EC 3.2.1.40), beta-rhamnosidase (EC 3.2.1.43), alpha-arabinopyranosidase (EC 3.2.1.-), beta-glucuronidase (EC 3.2.1.31), alpha-glucuronidase (EC 3.2.1.139), beta-xylosidase (EC 3.2.1.37) and alpha-xylosidase (EC 3.2.1.x).

The enzymes are classified according nomenclatures that are either based on the International Union of Biochemistry and Molecular Biology's Enzyme Nomenclature and Classification (http://www.chem.qmul.ac.uk/iubmb/enzyme/) or on Carbohydrate-Active EnZYmes (http://www.cazy.org/) database.

The term "activity" of an enzyme refers to the catalytic activity of the enzyme under appropriate conditions under which the enzyme serves as a protein catalyst, which converts specific polymeric or artificial substrates to specific oligomeric or monomeric products. In this context the term "appropriate conditions" is well known to and applicable by a person skilled in the art.

The "contacting" may be carried out by any measure known to a person skilled in the art as suitable for the inventive purpose. It is thereby preferred that the enzyme mixture is added to the biomass while stirring the biomass within the vessel. The enzyme(s) may also be immobilized on a carrier material.

In a preferred embodiment the hydrolysis of biomass is carried out for a time sufficient to hydrolyze at least 20 wt.-%, preferably at least 30 wt.-%, more preferred at least 50 wt.-% and most preferred at least 60 wt.-% of the biomass. Within a further preferred embodiment the hydrolysis of the biomass is carried out for a time sufficient to hydrolyze from 10 to 100 wt.-%, preferably from 20 to 90 wt.-% even more preferred from 30 to 85.0 wt.-% and most preferred from 40 to 75 wt.-% of the cellulose of the biomass. The term "hydrolyze" is to be understood as the hydrolytic conversion of insoluble polymeric components of the biomass to soluble monomeric, dimeric and/or oligomeric compounds by chemical, physical and/or enzymatic processes such as hydrolysis.

Within a particularly preferred embodiment the hydrolysis of biomass is carried out for 1 minute to 136 hours, more preferred for 30 minutes to 112 hours, particularly preferred for 1 hour to 100 hours, even more preferred for 4 hours to 96 hours also particularly preferred from 12 hours to 85 hours.

Within a further preferred embodiment the hydrolysis of biomass is carried out until the content of remaining insoluble solids is less than 40 wt.-%, preferably less than 30 wt.-%, even more preferred less than 20 wt.-% and most preferred less than 15 wt.-%. In a further preferred embodiment the hydrolysis of biomass is carried out until the content of remaining insoluble solids is from 5 to 40 wt.-%, preferably from 8 to 30 wt.-% and most preferred from 10 to 25 wt.-%.

Within another preferred embodiment the hydrolysis of biomass is carried out until the biomass is liquefied to at least 50%, preferably at least 60% and most preferred at least 80%, wherein a liquefaction of from 60 to 90% is particularly preferred.

The reaction temperature during hydrolysis is preferably selected from 25 to 80° C., more preferred selected from 30 to 75° C. and particularly preferred from 35 to 65° C. In another preferred embodiment the hydrolysis of biomass is carried out for 1 to 120 hours, preferably 2 to 110 hours, more preferred 3 to 100 hours, wherein the temperature is selected from 35 to 75° C. or from 45 to 65° C.

Within another preferred embodiment, the pH during hydrolysis is preferably selected from 4 to 6.5, particularly preferred from 4.5 to 5.5.

The appropriate dosage levels and operating conditions will be apparent to those of skill in the art, especially in light of the detailed disclosure provided herein. Optimum dosage levels will vary considerably depending upon the substrate and the pretreatment technologies used. The enzyme composition is preferably added to the biomass in an amount of from 0.01 to 24 wt.-% of the dry matter of the biomass, more preferred 0.025 to 12 wt.-% of the dry matter of the biomass, particularly preferred being 0.05 to 6 wt.-% of the dry matter of the biomass and most preferred from 0.1 to 3 wt.-% of the dry matter of the biomass. The total enzyme (protein) concentration was determined by the Bradford method with bovine serum albumin as a reference standard (Bradford, M., 1976).

The hydrolysis of biomass is carried out within any kind of vessel known to a person skilled in the art as suitable for the inventive process, preferably within a reactor. Suitable reactors are within the knowledge of a person skilled in the art. Preferable vessels/reactors include but are not limited to vessels/reactors comprising a stirring measure and/or a measure for pumping over or recirculating the biomass content within the reactor. Further preferred measures of preferred reactors include but are not limited to measures for temperature and/or pH-controlling and regulation of temperature and/or pH.

According to step b) of the inventive process, the temperature of the biomass hydrolysate is adjusted to a temperature selected from the range of from 50 to 95° C., preferably from the range of from 60 to 90° C., further preferred from the range of from 65 to 85° C. The adjustment is to be carried out by any measure known to a person skilled in the art as suitable for the inventive process.

Within a particularly preferred embodiment, the step b) of the inventive process is carried out for 1 minute to 120 minutes, preferably from 2 minutes to 90 minutes and particularly preferred from 3 minutes to 75 minutes whereas from 30 minutes to 90 minutes and from 45 minutes to 75 are also preferred.

According to step c) of the inventive process, at least one acid is added to the biomass hydrolysate to obtain a biomass hydrolysate-acid mixture. The at least one acid may be an organic or an inorganic acid. Within a preferred embodiment, the at least one acid is preferably selected from the group consisting of sulfuric acid, phosphoric acid, hydrochloric acid, nitric acid, acetic acid, formic acid, lactic acid, galacturonic acid, citric acid, succinic acid and mixtures thereof. Within a preferred embodiment, the at least one acid is selected from acids with a pKa value below 5.0, preferably from acids with a pKa value below 3.5, a pKa value from −4.0 to 5.0 is thereby particularly and from −3.0 to 5.0 is most preferred.

Within a further preferred embodiment, the at least one acid is added to the biomass hydrolysate until a pH of from 1.5 to 4.5, preferably from 2.0 to 4.0 and most preferred of from 2.5 to 3.5 of the biomass hydrolysate is reached.

Within a further preferred embodiment the temperature is selected from the range of from 65 to 85° C. and the pH from the range of 2.0 to 3.5. Within a further preferred embodiment the temperature is increased to 70° C. and the pH is set to 2.5.

Within another preferred embodiment, steps b) and c) of the inventive process are at least partially carried out concurrently. It is thereby particularly preferred that the at least one acid is added during the adjustment of the temperature of the biomass hydrolysate to a temperature selected from the range of from 60 to 90° C. from a temperature of 50° C. onwards, also preferred from a temperature of 60° C. onwards. It is further preferred that the at least one acid is added during the adjustment of the temperature of the biomass hydrolysate to a temperature selected from the range of from 65 to 85° C. from a temperature of 50° C. onwards, also preferred from a temperature of 60° C. onwards.

Within another preferred embodiment, the temperature of the at least one acid is selected from the range of from 5 to 50° C., preferably of from 10 to 40° C. and most preferred of from 15 to 30° C. and the at least one acid is added to the biomass hydrolysate at a temperature of the biomass hydrolysate selected from the range of from 50 to 95° C., preferably of from 65 to 85° C. It is thereby particularly preferred that the temperature difference between the at least one acid and the biomass hydrolysate is selected from the range of from 35 to 95%, preferably of from 40 to 90%.

It is also within the scope of the present invention that step c) of the inventive process is carried out before step b).

After the addition of the at least one acid to the biomass hydrolysate and the adjustment of the temperature of the biomass hydrolysate, the resulting composition is referred to as "biomass hydrolysate-acid mixture" within the scope of the present application.

According to step (d) of the inventive process a solid and a liquid phase are separated from the biomass hydrolysate-acid mixture. The separation of the solid and the liquid phase of the hydrolysate-acid mixture (in the following "liquid phase" or "liquid phase of the hydrolysate" are used synonymously with "liquid phase of the hydrolysate-acid mixture") may be carried out by any measure known to a person skilled in the art as suitable for the inventive purpose and is preferably carried out by filtration, centrifugation, decantation or pressing e.g. by a screw-press. Preferred is a filter press, most preferred a membrane filter press. In a preferred embodiment, the filter cloth of the filter press has a cloth air permeability of from 2 to 10 L/dm$^2$/min. Filtration aids such as diatomaceous earth or kieselguhr or perlite can also be added during the filtration, preferably in concentrations of from 0.1 wt.-% to 10wt.-%, more preferably between 0.5 wt.-% to 5 wt.-%, and most preferred between 1 wt.-% and 3 wt.-%.

After the separation of the solid and the liquid phase, deionization of the liquid phase according to step (e) is carried out. Deionization is preferably carried out by electrodialysis, capacitive deionization, membrane capacitive deionization, nanofiltration, reverse osmosis, chromatographic separation such as ion exchange chromatography, hydrophobic interaction chromatography and/or size exclusion chromatography or by any combination of two or more of these methods. "Membrane capacitive deionization" is performed by inserting a cation exchange membrane and an anion exchange membrane into the capacitive deionization unit.

Within particularly preferred embodiments, deionization is carried out either by standard electrodialysis or by electrodialysis using at least one bipolar membrane, particularly preferred followed by capacitive deionization, membrane capacitive deionization or ion exchange chromatography.

When using standard electrodialysis or electrodialysis using at least one bipolar membrane for the deionization, the ions removed from the solution are preferably recovered in a liquid called "concentrate". In this respect it is particularly preferred to add a liquid into a compartment of the electrodialysis unit before the start of the deionizaiton. In a further preferred embodiment, this liquid is not replaced after stopping the deionization of a given volume, but the concentrate is reused in repeated deionizations over at least 2 cycles, more preferred at least 4 cycles, particularly preferred 6 cycles and most preferred 10 cycles.

Within the present invention "electrodialysis using at least one bipolar membrane" is to be understood as any technique comprising the use of three different types of membranes suitable to remove salts by removing ions such as e.g. Na+, K+, Mg2+, Ca2+, SO42−, PO33−, Cl− and split H2O present in the liquid phase. Electrodialysis using at least one bipolar membrane preferably comprises the use of a cation exchange membrane, an anion exchange membrane and a catalytic intermediate layer, a so-called "bipolar membrane", to enable the splitting of the water within the liquid phase into protons and hydroxide ions. Through the combination of the selective removal of salts by the cation and anion exchange membranes with the simultaneous water dissociation on the catalytic intermediate layer, acid and base fractions are formed.

Within a preferred embodiment, at least one cation exchange membrane, at least one anion exchange membrane and at least one catalytic intermediate layer or bipolar membrane are used. Within a further preferred embodiment, at least two sets of these membranes are arranged in series, preferably at least 4 sets, further preferred at least 6 sets and most preferred at least 10 sets. Within a particularly preferred embodiment, all three membranes or all sets of membranes as defined before are arranged within a single device.

The deionization is preferably carried out at a temperature within the range of from 5° C. to 80° C., more preferred within the range of from 10° C. to 75° C., most preferred within the range of from 15° C. to 70° C. The pressure drop through the electrodialysis cell is preferably below 1 bar, more preferred below 0.5 bar. Within a further particularly preferred embodiment, deionization is carried out until the conductivity of the solution is reduced to at least 10 mS/cm, more preferred to at least 6 mS/cm particularly preferred to at least 4 mS/cm and most preferred to at least 2 mS/cm.

In a further preferred embodiment, the deionization by electrodialysis using at least one bipolar membrane is followed by capacitive deionization. The capacitive deionization is preferably applied as so-called "membrane capacitive deionization", i.e. by inserting a cation exchange membrane and an anion exchange membrane into the capacitive deionization unit. If the electrodialysis using at least one bipolar membrane is followed by membrane capacitive deionization, the electrodialysis is preferably performed until the conductivity of the solution is reduced to at least 10 mS/cm, more preferred to at least 6 mS/cm particularly preferred to at least 4 mS/cm and most preferred to at least 2 mS/cm before switching to membrane capacitive deionization. The membrane capacitive deionization following the electrodialysis is then used to further decrease the conductivity of the solution preferably to at least 8 mS/cm, more preferred to at least 6 mS/cm, particularly preferred to at least 4 mS/cm and most preferred to at least 2 mS/cm.

In a further preferred embodiment, the deionization by electrodialysis using at least one bipolar membrane is followed by ion exchange chromatography. If the electrodialysis using at least one bipolar membrane is followed by ion exchange chromatography, the electrodialysis is preferably performed until the conductivity of the solution is reduced to at least 10 mS/cm, more preferred to at least 6 mS/cm particularly preferred to at least 4 mS/cm and most preferred to at least 2 mS/cm before switching to membrane capacitive deionization. The ion exchange chromatography following the electrodialysis is then used to further decrease the conductivity of the solution preferably to at least 8 mS/cm, more preferred to at least 6 mS/cm, particularly preferred to at least 4 mS/cm and most preferred to at least 2 mS/cm.

Within the present invention, "ion exchange" is defined as an exchange of ions between a solution containing at least one ion and a solid polymeric or mineralic ion exchange material, wherein an ion dissolved in the solution is exchanged and replaced through contact with the ion exchange material by an ion of the same charge.

Deionization by electrodialysis using at least one bipolar membrane reduces the waste produced during the deionization as well as the process costs in other applications. The use of electrodialysis using at least one bipolar membrane leads to the production of a base fraction, which can be used e.g. as pH agent in the production of enzymes, in the hydrolysis of the biomass or for the pretreatment of the biomass. Within a preferred embodiment, the base fraction produced has a pH of from 9 to 14, more preferred from 12 to 13. The use of electrodialysis using at least one bipolar membrane also leads to the production of an acid fraction, which can be used e.g. for the hydrolysis of biomass or for the pretreatment of the biomass or for step c) of the inventive process. Within a preferred embodiment, the acid fraction produced has a pH of from 1 to 5, more preferred from 2 to 4. Particularly preferred is the usage of the acid fraction for the steam explosion. Most preferred is the addition of the acid fraction to the biomass hydrolysate according to step c) of the inventive process. The deionization by electrodialysis is preferably carried out with the liquid phase at a temperature within the range of 5° C. to 80° C., more preferred within 10° C. to 75° C., most preferred within 15° C. to 70° C. The pressure drop through the electrodialysis cell is preferably below 1 bar, more preferred below 0.5 bar. Within a further particularly preferred embodiment, deionization is carried out either by standard electrodialysis or by electrodialysis using at least one bipolar membrane until the conductivity of the solution is reduced to 10 mS/cm, more preferred to 6 mS/cm particularly preferred to 4 mS/cm and most preferred to 2 mS/cm. In a further preferred embodiment, the deionization is then further continued by capacitive deionization, membrane capacitive deionization or ion exchange chromatography.

In a preferred embodiment, the ion exchange resins used in the ion exchange chromatography step are one cation exchange resin and one anion exchange resin. In a further preferred embodiment, the anion exchange resin and the cation exchange resin are used in subsequent ion exchange steps. Particularly preferred anion exchange resins are anion exchange resins with tertiary amine functional groups. The anion exchange resin matrix is preferably a styrene divinylbenzene copolymer or a crosslinked acrylic gel structure. Further preferred are anion exchange resins in the OH− form. Particularly preferred cation exchange resins are cation exchange resins with sulfonate or carboxylic acid functional groups. The cation exchange resin matrix is preferably a styrene divinylbenzene copolymer or a crosslinked acrylic structure. Further preferred are cation exchange resins in the H+ form. In a preferred embodiment, the ion exchange resins have a capacity of at least 0.5 eq/L resin, more preferred at least 1 eq/L resin, most preferred at least 2 eq/L resin. 1 eq is defined as 1 mol of the ion to be exchanged by the resin divided by the valence of this ion.

When bringing into contact the cation exchange resin with the liquid, the liquid should be at a temperature from 5° C. to 135° C., preferably between 10° C. and 70° C. When bringing into contact the anion exchange resin with the liquid, the liquid should be at a temperature from 5° C. to 75° C., preferably between 10° C. and 60° C.

In a preferred embodiment, the contact time of each contact between the ion exchange resin and the liquid should be between 0.1 and 300 min, more preferred between 0.2 and 100 min, most preferred between 0.3 and 10 min.

The cation exchange resin is regenerated using an acid, preferably sulfuric acid, nitric acid, phosphoric acid or hydrochloric acid. The acid used should be concentrated, preferably at a concentration between 0.05 and 20 M, most preferably between 0.5 and 10 M. The regeneration of the cation exchange resin is preferably performed at least 15° C. The anion exchange resin is regenerated using a base, preferably sodium hydroxide, sodium carbonate or ammonium carbonate. The base used should be concentrated, preferably at a concentration between 0.05 and 20 M, most preferably between 0.5 and 10 M. The regeneration of the anion exchange resin is preferably performed at least 15° C. The contact time of the ion exchange resin and the base or the acid should preferably be at least 5 min, more preferably at least 15 min. The cation and anion exchange resins are preferably used over at least 500 deionization-regeneration cycles, more preferably over at least 1500 cycles.

In a preferred embodiment, the ion exchange chromatography is performed in a fixed bed or in a loose bed within a chromatography column. The ion exchange according to the present invention will however not be carried out in a simulated moving bed setup. Simulated moving bed setups are only used when species with very similar properties have to be separated from each other, as for example two sugar monomers in case of a separation of for example glucose and xylose. Within the method of the present invention, however, salts are removed from the liquid, i.e. ions (charged species) are separated from the rest of the components (non-charged species). As these two classes of components to be separated from each other differ significantly in their basic physical properties, the simulated moving bed setup is not suitable for the method of the present invention. Furthermore, as a simulated moving bed setup is a rather complex and expensive setup, the preferred embodiment using a fixed bed or a loose bed within a chromatography column provides further advantages.

In a further preferred embodiment, the anion exchange resin and the cation exchange resin are in two different columns and not mixed. In a further preferred embodiment, the liquid to be deionized is first brought into contact with the cation exchange resin and then with the anion exchange resin. A further preferred embodiment consist in bringing the liquid in contact with the cation exchange resin, then with the anion exchange resin and then again with fresh cation exchange resin or with the cation exchange resin that has already been used in the first step. A further preferred embodiment consist in repeating cycles of cation exchange resin and anion exchange resin. The ion exchange resin used in the repeated cycles can either be fresh ion exchange resin or ion exchange resin that has already been used in a previous cycle. The number of repeated contact cycles between the ion exchange resin and the liquid is preferably between 1 and 10, most preferably between 2 and 5.

When bringing into contact the liquid with the ion exchange resin in a column, the flow rate should preferably be between 1 to 200 bed volumes per hour, more preferably between 2 to 80 bed volumes per hour.

In a further preferred embodiment, the ion exchange chromatography is performed in a stirred tank.

Within a further particularly preferred embodiment, at least one adsorbent is added before or during any of the steps (b), (c) or (d). The at least one adsorbent is preferably selected from the group consisting of bentonite, charcoal, activated carbon, diatomaceous earth or kieselguhr, perlite, bleaching earth, clay minerals, polymeric resins and any mixture thereof.

Carrying out steps a) to e) of the inventive process will lead to a composition which is referred to as "purified hydrolysate" within the scope of the present application.

Another aspect of the present invention pertains to a purified hydrolysate prepared according to the inventive process as defined herein. The salt content of the purified hydrolysate is preferably at most 80%, preferably at most 60%, more preferred at most 40%, more preferred at most 20%, and most preferred at most 10% all relative to the salt content after hydrolysis of the substrate.

The present invention further pertains to the use of the purified hydrolysate prepared according to the inventive process as a fermentation medium.

Valuable organic compounds resulting from bacterial fermentation of the purified hydrolysate comprise but are not limited to organic acids (such as acetic acid, lactic acid, succinic acid, itaconic acid, fumaric acid, propionic acid, and glucuronic acid), amino acids (such as glutamic acid, leucine, lysine, threonine, aspartic acid, phenylalanine, cysteine), caprolactams (such as alpha-amino-caprolactam), antibiotics (such as bleomycin, virginiamycin, lincomycin, monensin, blasticidin, tetracycline), vitamins (such as vitamin B2, B12 and C), enzymes, nucleotides/nucleosides (such as NADH, ATP, cAMP, FAD, coenzyme A), biogas, biopolymers (such as polyhydroxybutyrate, polyamides/fibroins), proteins, polysaccharides (such as xanthan, dextran), amino glucans (such as hyaluronic acid) as well as organic solvents and biofuels (such as acetone, ethanol, butanol, propanediol).

Valuable organic compounds resulting from yeast fermentation of the purified hydrolysate comprise but are not limited to organic solvents (e.g. ethanol, propanol), nucleotides (e.g. RNA), biosurfactants (e.g. sophorose lipids), enzymes and biopolymers (e.g. spidroins).

Valuable organic compounds resulting from fungal fermentation of the purified hydrolysate comprise organic acids (such as citric acid, fumaric acid, itaconic acid), antibiotics (such as penicillin, cephalosporin), enzymes, and polysaccharides (such as chitin).

In a further preferred embodiment of this process the organic compound is selected from alcohols, organic acids, biopolymers, antibiotics, amino acids, caprolactams, polysaccharides, organic solvents, biofuels, aminoglucans, nucleotides/nucleosides, vitamins, biosurfactants, enzymes and mixtures thereof.

In the following particularly preferred embodiments of the inventive process are described which are not to be understood as limiting the invention in any respect.

Particularly Preferred Embodiment 1

Particularly preferred is a process for the purification of biomass hydrolysate comprising the steps
a) Providing a biomass hydrolysate;
b) Adjusting the temperature of the biomass hydrolysate to a temperature selected from the range of from 50 to 95° C., preferably from 30 to 90° C., particularly preferred from 45 to 75° C. and most preferred to 70° C.;
c) Addition of at least one acid to the biomass hydrolysate;
d) Solid-liquid separation of the biomass hydrolysate-acid mixture to obtain a solid phase and a liquid phase;
e) Deionization of the liquid phase of the hydrolysate-acid mixture after separation according to step d);
wherein the biomass is a lignocellulosic substrate, preferably cereal straw or bagasse, particularly preferred pretreated cereal straw or bagasse.

Particularly Preferred Embodiment 2

Process as defined for particularly preferred embodiment 1 wherein step b) is carried out for 1 to 90 minutes, preferably for 2 to 75 minutes.

Particularly Preferred Embodiment 3

Process as defined for particularly preferred embodiment 1 or 2 wherein the acid is an organic acid, preferably sulphuric acid and the pH of the hydrolysate is adjusted to from 2.0 to 3.0.

Particularly Preferred Embodiment 4

Process as defined for any of particularly preferred embodiments 1 to 3 wherein step c) is carried out after step b).

Particularly Preferred Embodiment 5

Process as defined for any of particularly preferred embodiments 1 to 4 wherein the solid-liquid separation is carried out by a filter press, preferably by a membrane filter press.

Particularly Preferred Embodiment 6

Process as defined for any of particularly preferred embodiments 1 to 5 wherein deionization is carried out by electrodialysis.

Particularly Preferred Embodiment 7

Process as defined for any of particularly preferred embodiments 1 to 6 wherein deionization is carried out by electrodialysis followed by an ion exchange chromatography step or by membrane capacitive deionization.

Particularly Preferred Embodiment 8

Process as defined for any of particularly preferred embodiments 1 to 7 wherein deionization is carried out by electrodialysis using at least one bipolar membrane.

Particularly Preferred Embodiment 9

Process as defined for any of particularly preferred embodiments 1 to 6 or 8 wherein deionization is carried out by electrodialysis using at least one bipolar membrane followed by an ion exchange chromatography step or by membrane capacitive deionization.

Particularly Preferred Embodiment 10

Process as defined for any of particularly preferred embodiments 5 to 9 wherein deionization by electrodialysis is preferably carried out at a temperature within the range of 5° C. to 80° C., more preferred within 10° C. to 75° C., most preferred within 15° C. to 70° C.

Particularly Preferred Embodiment 11

Process as defined for any of particularly preferred embodiments 5 to 10 wherein deionization is carried out by electrodialysis and the pressure drop through the electrodialysis cell is preferably below 1 bar, more preferred below 0.5 bar.

Particularly Preferred Embodiment 12

Process as defined for any of particularly preferred embodiments 1 to 4 wherein deionization is carried out by ion exchange chromatography preferably with cation exchange before anion exchange.

Particularly Preferred Embodiment 13

Particularly preferred is a process for the purification of biomass hydrolysate comprising the steps
  a) Providing a biomass hydrolysate from pretreated cereal straw or bagasse;
  b) Adjusting the temperature of the biomass hydrolysate to a temperature selected from the range of from 30 to 90° C. for 2 to 75 minutes;
  c) Addition of at least one organic acid to the biomass hydrolysate to adjust the pH to from 2.0 to 3.0;
  d) Solid-liquid separation of the biomass hydrolysate-acid mixture to obtain a solid phase and a liquid phase by a membrane filter press;
  e) Deionization of the liquid phase of the hydrolysate-acid mixture after separation according to step d) wherein deionization is carried out by electrodialysis followed by an ion exchange chromatography step or by membrane capacitive deionization.

Particularly Preferred Embodiment 14

Particularly preferred is a process for the purification of biomass hydrolysate comprising the steps
  a) Providing a biomass hydrolysate from pretreated cereal straw or bagasse;
  b) Adjusting the temperature of the biomass hydrolysate to a temperature selected from the range of from 30 to 90° C. for 2 to 75 minutes;
  c) Addition of at least one organic acid to the biomass hydrolysate to adjust the pH to from 2.0 to 3.0;
  d) Solid-liquid separation of the biomass hydrolysate-acid mixture to obtain a solid phase and a liquid phase by a membrane filter press;
  e) Deionization of the liquid phase of the hydrolysate-acid mixture after separation according to step d)
wherein deionization is carried out by ion exchange chromatography with cation exchange before anion exchange.

Particularly Preferred Embodiment 15

Particularly preferred is a process for the purification of biomass hydrolysate comprising the steps
  a) Providing a biomass hydrolysate from pretreated cereal straw or bagasse;
  b) Adjusting the temperature of the biomass hydrolysate to a temperature selected from the range of from 30 to 90° C. for 2 to 75 minutes;
  c) Addition of at least one organic acid to the biomass hydrolysate to adjust the pH to from 2.0 to 3.0;
  d) Solid-liquid separation of the biomass hydrolysate-acid mixture to obtain a solid phase and a liquid phase by a membrane filter press;
  e) Deionization of the liquid phase of the hydrolysate-acid mixture after separation according to step d);
wherein deionization is carried out by ion exchange chromatography with cation exchange before anion exchange.

Particularly Preferred Embodiment 16

Particularly preferred is a process for the purification of biomass hydrolysate comprising the steps
  a) Providing a biomass hydrolysate from pretreated cereal straw or bagasse;
  b) Adjusting the temperature of the biomass hydrolysate to a temperature selected from the range of from 30 to 90° C. for 2 to 75 minutes;
  c) Addition of at least one organic acid to the biomass hydrolysate to adjust the pH to from 2.0 to 3.0;
  d) Solid-liquid separation of the biomass hydrolysate-acid mixture to obtain a solid phase and a liquid phase by a membrane filter press;
  e) Deionization of the liquid phase of the hydrolysate-acid mixture after separation according to step d);
wherein deionization is carried out by ion exchange chromatography with cation exchange before anion exchange and
wherein an additive is added before adjusting the temperature according to step b).

Particularly Preferred Embodiment 17

Particularly preferred is a process for the purification of biomass hydrolysate comprising the steps
  a) Providing a biomass hydrolysate from pretreated cereal straw or bagasse;
  b) Adjusting the temperature of the biomass hydrolysate to a temperature selected from the range of from 30 to 90° C. for 2 to 75 minutes;
  c) Addition of at least one organic acid to the biomass hydrolysate to adjust the pH to from 2.0 to 3.0;
  d) Solid-liquid separation of the biomass hydrolysate-acid mixture to obtain a solid phase and a liquid phase by a membrane filter press;
  e) Deionization of the liquid phase of the hydrolysate-acid mixture after separation according to step d);
wherein deionization is carried out by ion exchange chromatography with cation exchange before anion exchange and wherein an additive is added after adjusting the pH according to step c).

EXAMPLES AND FIGURES

The present invention is now described by the following example and figures. The example and figures are for illustrative purposes only and are not to be understood as limiting the invention.

EXAMPLE 1

Cereal straw with a dry matter content of 45 wt.-% was pre-treated by steam explosion (220° C.). After the steam explosion, the so pretreated cereal straw ("substrate") was introduced into a stirred tank (Labfors, Infors AG, Switzerland). An enzyme composition containing 91.3 wt.-% Celluclast® (Cellulase from *Trichoderma reesei* ATCC 26921, C2730 Sigma) and 8.7 wt.-% Glucosidase (49291 Sigma) was added to the substrate at an enzyme to solid ratio of 0.5 wt.-% to hydrolyze the substrate to obtain a slurry. The hydrolysis was carried out at 50° C., pH 5.0 for 72 hours with stirring at 50 rpm. After the hydrolysis, the slurry was heated to 70° C. for 1 h while stirring at 200 rpm and then the pH was set to 2.5 using 1 M $H_2SO_4$. The so-treated slurry was then filtered using a filter press with filter cloth having a cloth air permeability of 5 $L/dm^2/min$ at a constant pressure of 3 bar to obtain a liquid and a solid phase. 200 mL of the liquid phase was then deionized using ion exchange resins: the liquid was pumped into a glass column (XK16, GE Healthcare) containing 30 g cation exchange resin (Lewatit® S8528, Lanxess) at a pumping rate of 5 mL/min and at room temperature. After the cation exchange column, the resulting liquid phase was pumped into a glass column (XK16, GE Healthcare) containing 30 g anion exchange resin (Lewatit® S6368 A, Lanxess) at a pumping rate of 5 mL/min and at room temperature. The same deionization was performed with hydrolysate that was not treated with a heating step and a pH shift to pH 2.5 (i.e. state of the art process). The improved purification procedure was demonstrated by two means: (1) the deionization efficiency and (2) the fouling on the IEX resin.

Figure 1:
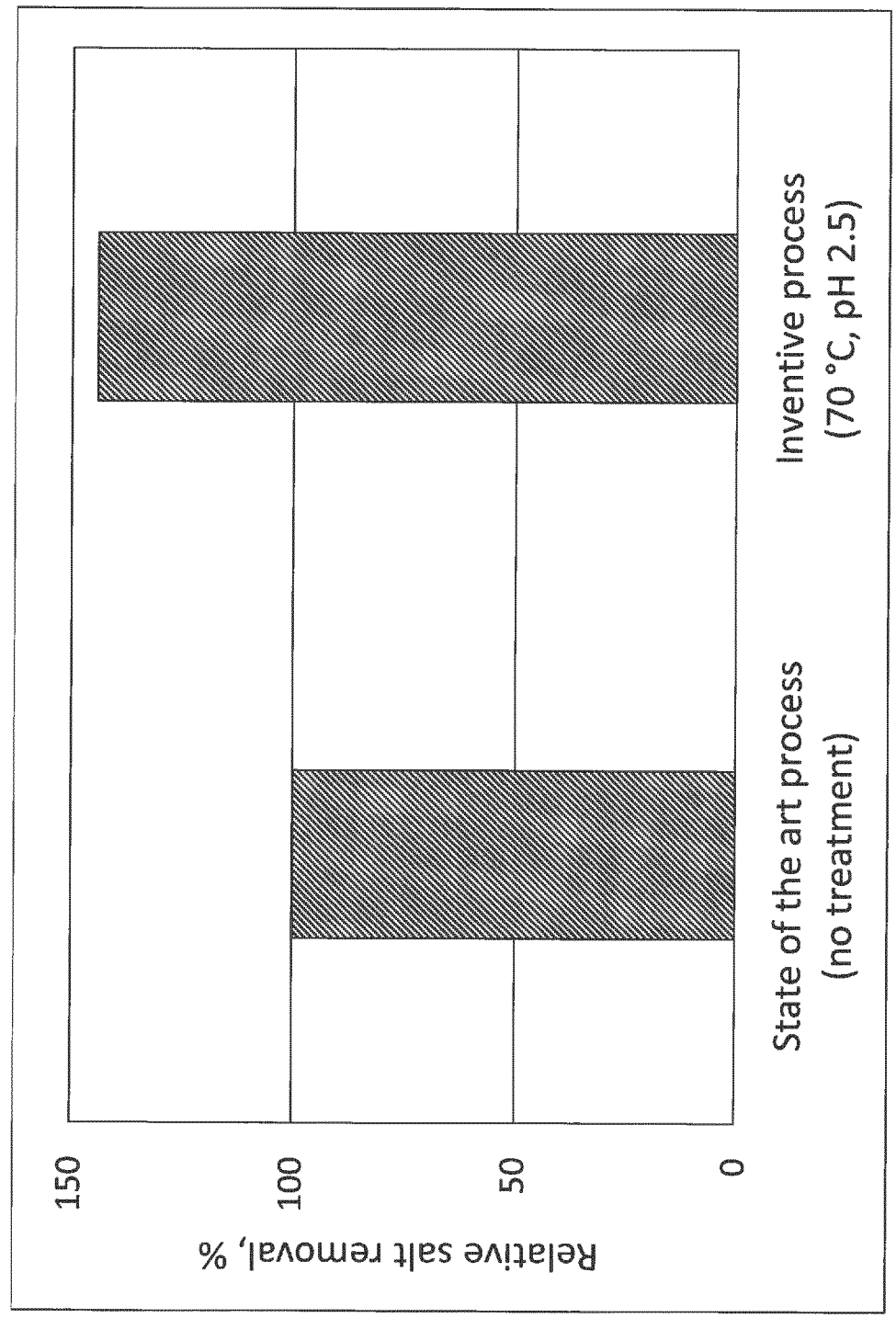
FIG. 1 shows the relative increase of salt removal after ion exchange chromatography of non-treated hydrolysate (left column) and after ion exchange chromatography of treated hydrolysate (inventive process: heating to 70° C., followed by a pH shift to 2.5) (right column) when carrying out the process of the present invention according to example 1.

The deionization efficiency in both assays was determined by measuring the amount of salts removed from the liquid phase of the hydrolysate. The results are shown in FIG. 1. The comparison shows a significant increase in salt removal for the liquid phase of the hydrolysate which was treated with the heating step and the pH shift, relative to the salt removal of the non-treated liquid phase of the hydrolysate (state of the art process).

Figure 2:
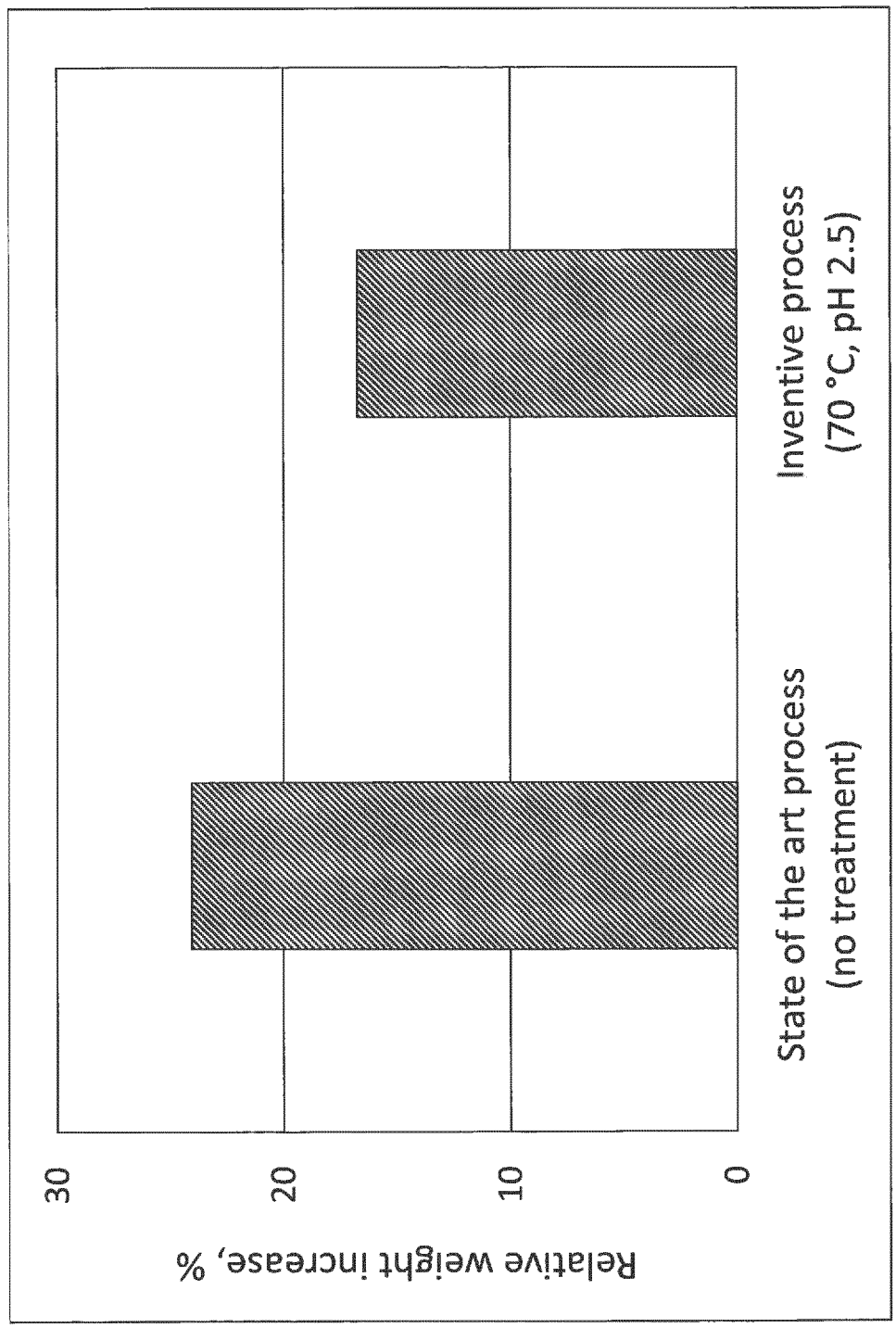
FIG. 2 shows the relative increase of weight of the anion exchange resin after ion exchange chromatography of non-treated hydrolysate (left column) and after ion exchange chromatography of treated hydrolysate (inventive process: heating to 70° C., followed by a pH shift to 2.5) (right column) when carrying is out the process of the present invention according to example 1.

The fouling of the anion exchange resin in both assays was determined by comparing the increase of weight of the anion exchange resin before and after the deionization. The results are shown in FIG. 2. The comparison of this value between both assays indicates a stronger fouling by 30.3% on the resin that was brought into contact with the non-treated hydrolysate (produced according to the state of the art process).

EXAMPLE 2

Cereal straw with a dry matter content of 45 wt.-% was pretreated by steam explosion (220° C.). After the steam explosion, the so pretreated cereal straw ("substrate") was introduced into a stirred tank (Labfors, Infors AG, Switzerland). An enzyme composition containing 91.3 wt.-% Celluclast® (Cellulase from *Trichoderma reesei* ATCC 26921, C2730 Sigma) and 8.7 wt.-% Glucosidase (49291 Sigma) was added to the substrate at an enzyme to solid ratio of 0.5 wt.-% to hydrolyze the substrate to obtain a slurry. The hydrolysis was carried out at 50° C., pH 5.0 for 72 hours with stirring at 50 rpm. After the hydrolysis, 2 wt.-% bentonite (Tonsil® 210 FF, Clariant Produkte (Deutschland) GmbH) were added to the slurry and the mixture was stirred at 200 rpm for 1 h at room temperature. Then the slurry was heated to 70° C. for 1 h while stirring at 200 rpm and then the pH was set to 2.5 using 1 M $H_2SO_4$. The so treated slurry was then filtered using a filter press with filter cloth having a cloth air permeability of 5 $L/dm^2/min$ at a constant pressure of 3 bar to obtain a liquid and a solid phase. 200 mL of the liquid phase was then deionized using ion exchange resins: the liquid was pumped into a glass column (XK16, GE Healthcare) containing 30 g cation exchange resin (Lewatit® S8528, Lanxess) at a pumping rate of 5 mL/min and at room temperature. After the cation exchange column, the resulting liquid phase was pumped into a glass column (XK16, GE Healthcare) containing 30 g anion exchange resin (Lewatit® S6368 A, Lanxess) at a pumping rate of 5 mL/min and at room temperature. The same deionization was performed with hydrolysate that was not treated with bentonite, with a heating step and a pH shift to pH 2.5 (i.e. state of the art process). The improved purification procedure was demonstrated by two means: (1) the deionization efficiency and (2) the fouling on the IEX resin.

Figure 3:
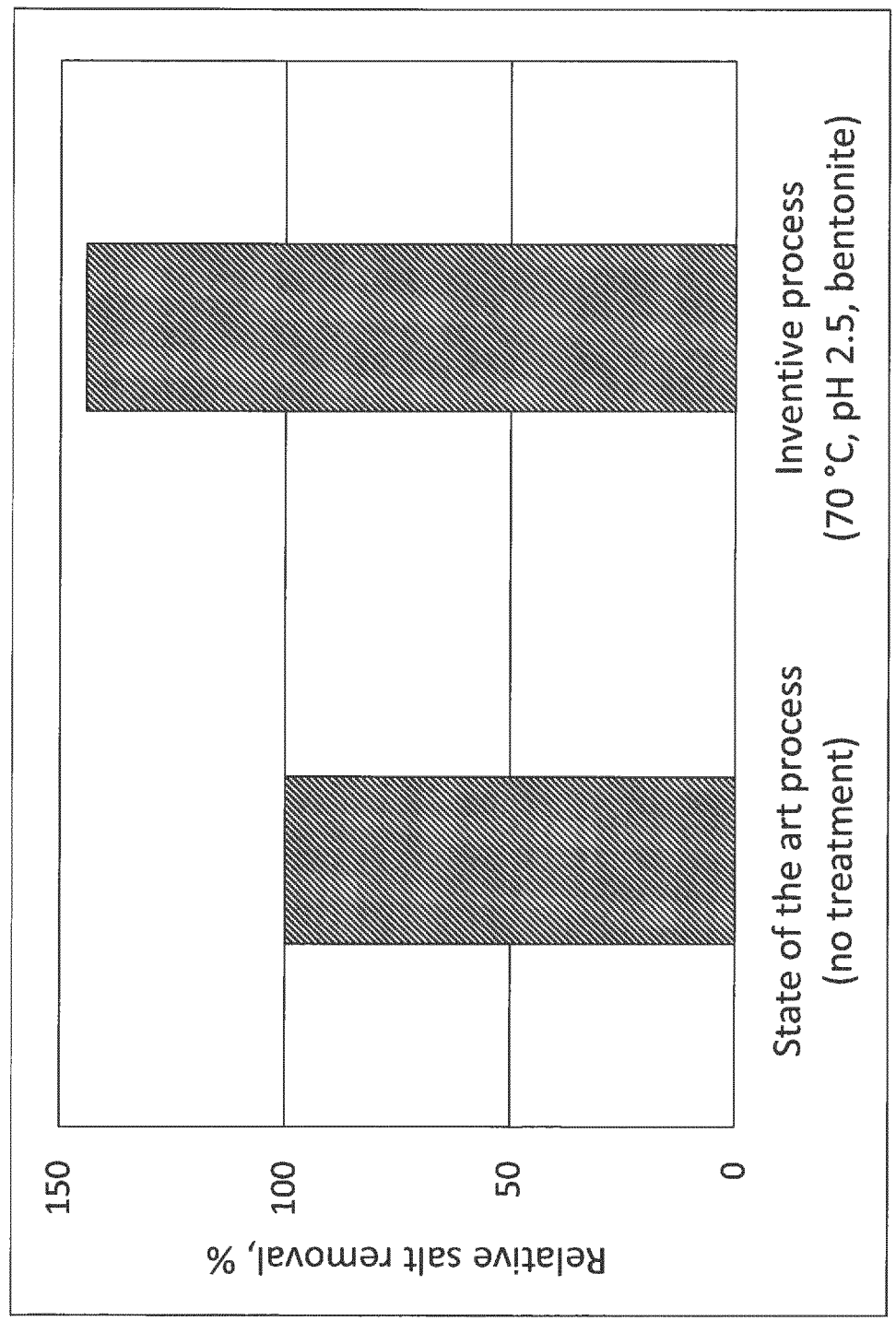
FIG. 3 shows the relative increase of salt removal after ion exchange chromatography of non-treated hydrolysate (left column) and after ion exchange chromatography of treated hydrolysate (inventive process: addition of bentonite, heating to 70° C., followed by a pH shift to 2.5) (right column) when carrying out the process of the present invention according to example 2.

The deionization efficiency in both assays was determined by measuring the amount of salts removed from the liquid phase of the hydrolysate. The results are shown in FIG. 3. The comparison shows a significant increase in the salt removal for the liquid phase of the hydrolysate that was treated with bentonite, with the heating step, and with the pH shift, relative to the salt removal of the non-treated liquid phase of the hydrolysate (state of the art process).

Figure 4:
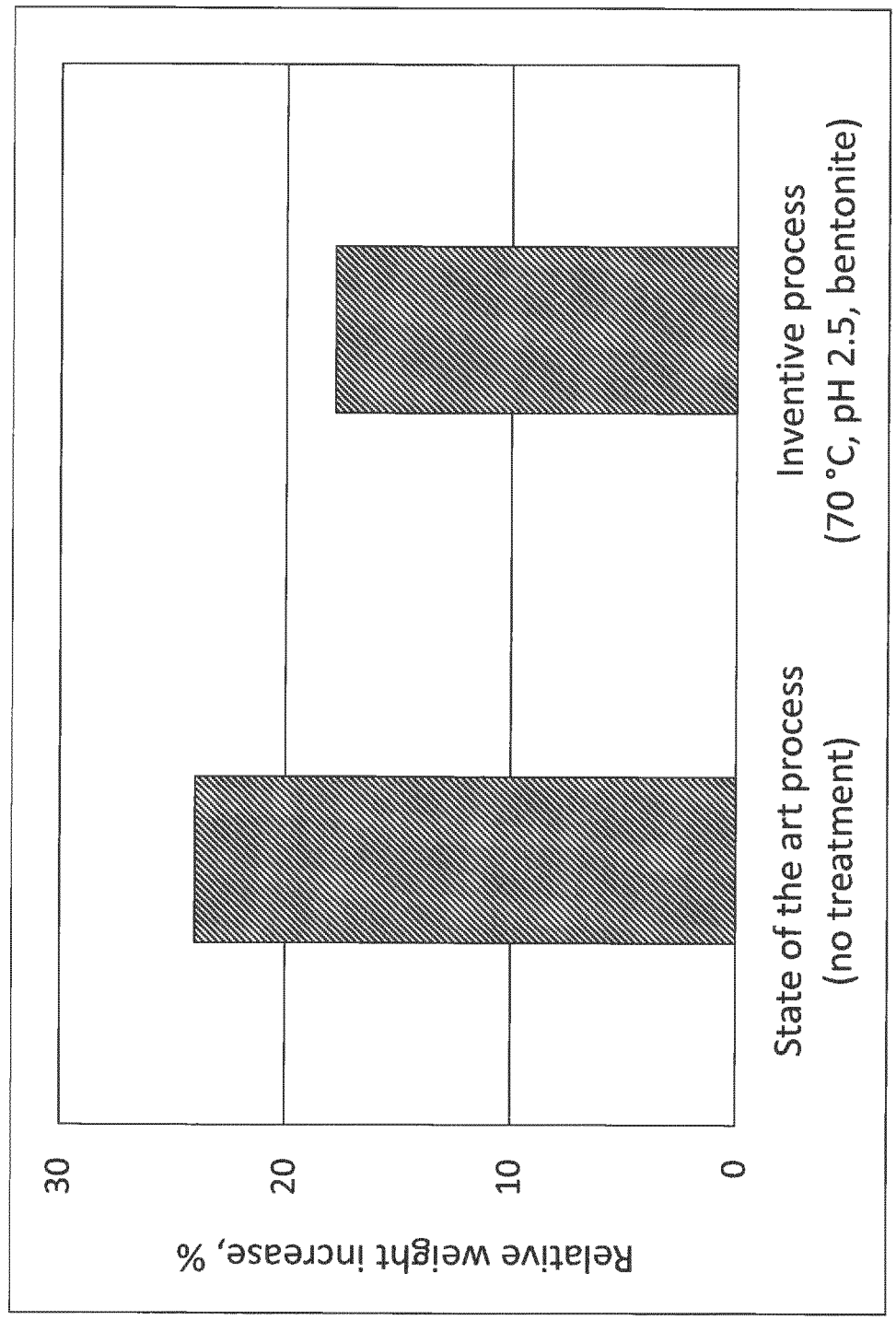
FIG. 4 shows a the relative increase of weight of the anion exchange resin after ion exchange chromatography of non-treated hydrolysate (left column) and after ion exchange chromatography of treated hydrolysate (inventive process: addition of bentonite, heating to 70° C., followed by a pH shift to 2.5) (right column) when carrying out the process of the present invention according to example 2.

The fouling of the anion exchange resin in both assays was determined by comparing the increase of weight of the anion exchange resin before and after the deionization. The results are shown in FIG. 4. The comparison of this value between both assays indicates a stronger fouling by 26.5% on the resin that was brought into contact with the non-treated hydrolysate (produced according to the state of the art process).

EXAMPLE 3

Cereal straw with a dry matter content of 45 wt.-% was pretreated by steam explosion (220° C.). After the steam explosion, the so pretreated cereal straw ("substrate") was introduced into a stirred tank (Labfors, Infors AG, Switzerland). An enzyme composition containing 91.3 wt.-% Celluclast® (Cellulase from *Trichoderma reesei* ATCC 26921, C2730 Sigma) and 8.7 wt.-% Glucosidase (49291 Sigma) was added to the substrate at an enzyme to solid ratio of 0.5 wt.-% to hydrolyze the substrate to obtain a slurry. The hydrolysis was carried out at 50° C., pH 5.0 for 72 hours with stirring at 50 rpm. After hydrolysis, the slurry was heated to 70° C. for 1 h while stirring at 200 rpm and then the pH was set to 2.5 using 1 M $H_2SO_4$. Then 2 wt.-% kieselguhr (Becogur® 200, Eaton) was added to the slurry and stirred at 200 rpm for 1 h at room temperature. The so treated slurry was then filtered using a filter press with filter cloth having a cloth air permeability of 5 L/dm$^2$/min at a constant pressure of 3 bar to obtain a liquid and a solid phase. The liquid phase was then deionized using ion exchange resins: the liquid was poured into a stirred glass tank (Multifors, Infors AG) and 15wt.-% cation exchange resin (Lewatit® S8528, Lanxess) was added at room temperature. The mixture was stirred for 1 h at 200 rpm. Then, the cation exchange resin was removed through filtration of the mixture using a paper filter (Black ribbon 589/1, Whatman). The resulting liquid phase was again poured into a stirred glass tank (Multifors, Infors AG) and 15wt.-% anion exchange resin (Lewatit® S6368 A, Lanxess) was added at room temperature. The mixture was stirred for 1 h at 200 rpm. Then, the anion exchange resin was removed through filtration of the mixture using a paper filter (Black ribbon 589/1, Whatman). The same deionization was performed with hydrolysate that was not treated with a heating step and a pH shift to pH 2.5, followed by addition of kieselguhr ("state of the art" process). The improved purification procedure was demonstrated by two means: (1) the deionization efficiency and (2) the fouling on the IEX resin.

Figure 5:
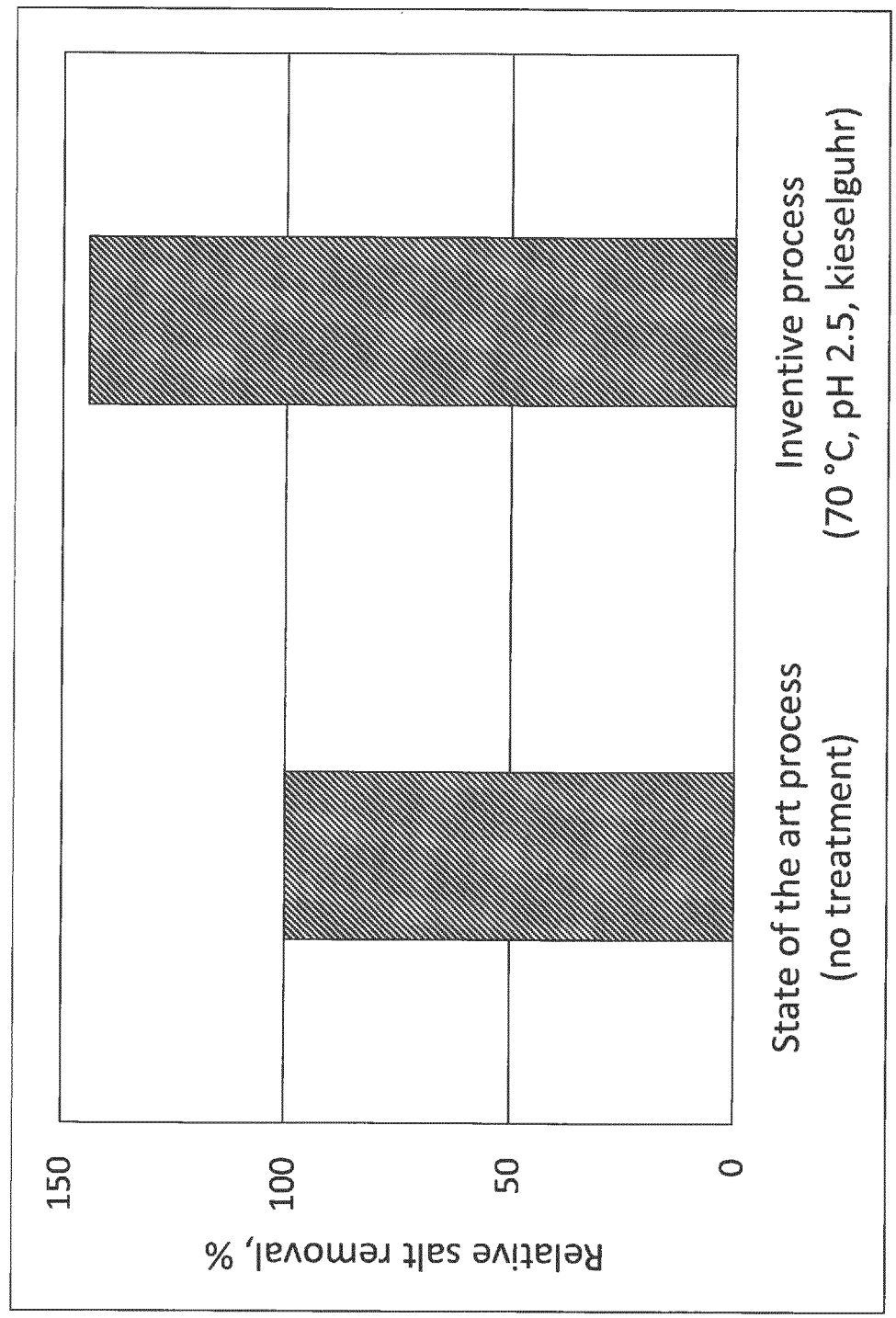
FIG. 5 shows the relative increase of salt removal after ion exchange chromatography of non-treated hydrolysate (left column) and after ion exchange chromatography of treated hydrolysate (inventive process: heating to 70° C., followed by a pH shift to 2.5 and addition of kieselguhr) (right column) when carrying out the process of the present invention according to example 3.

The deionization efficiency in both assays was determined by measuring the amount of salts removed from the liquid phase of the hydrolysate. The results are shown in FIG. 5. The comparison shows a significant increase in the salt removal for the liquid phase of the hydrolysate that was treated with the heating step and with the pH shift, followed by the addition of kieselguhr, relative to the salt removal of the non-treated liquid phase of the hydrolysate (state of the art process).

Figure 6:
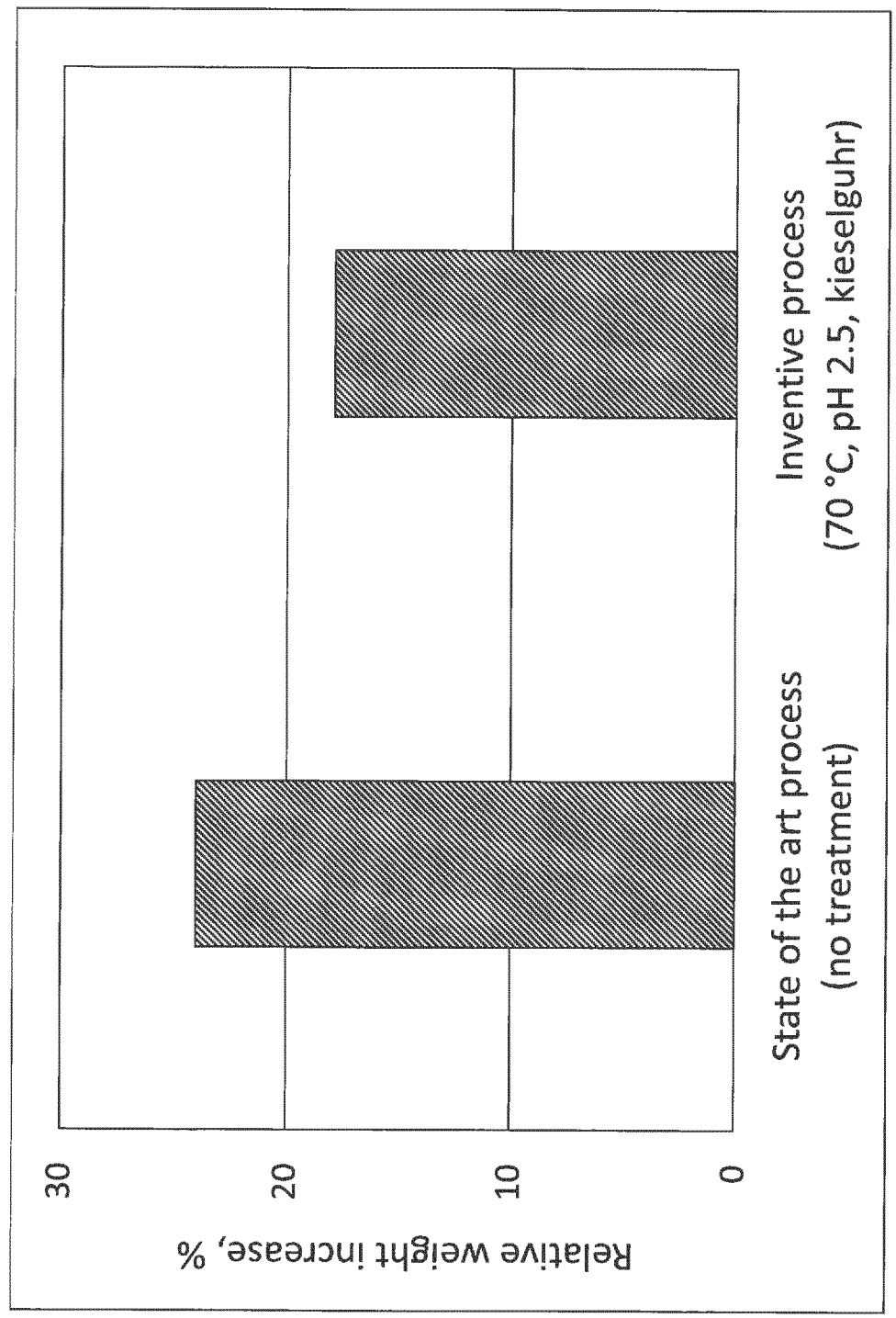
FIG. 6 shows the relative increase of weight of the anion exchange resin after ion exchange chromatography of non-treated hydrolysate (left column) and after ion exchange chromatography of treated hydrolysate (inventive process: heating to 70° C., followed by a pH shift to 2.5 and addition of kieselguhr) (right column) when carrying out the process of the present invention according to example 3.

The fouling of the anion exchange resin in both assays was determined by comparing the increase of weight of the anion exchange resin before and after the deionization. The results are shown in FIG. 6. The comparison of this value between both assays indicates a stronger fouling by 26.4% on the resin that was brought into contact with the non-treated hydrolysate (produced according to the state of the art process).

EXAMPLE 4

Cereal straw with a dry matter content of 45 wt.-% was pretreated by steam explosion (220° C.). After the steam explosion, the so pretreated cereal straw ("substrate") was introduced into a stirred tank (Labfors, Infors AG, Switzerland). An enzyme composition containing 91.3 wt.-% Celluclast® (Cellulase from *Trichoderma reesei* ATCC 26921, C2730 Sigma) and 8.7 wt.-% Glucosidase (49291 Sigma) was added to the substrate at an enzyme to solid ratio of 0.5 wt.-% to hydrolyze the substrate to obtain a slurry. The hydrolysis was carried out at 50° C., pH 5.0 for 72 hours with stirring at 50 rpm. After hydrolysis, the slurry was heated to 70° C. for 1 h while stirring at 200 rpm and then the pH was set to 2.5 using 1 M $H_2SO_4$. The so-treated slurry was then filtered using a filter press with filter cloth having a cloth air permeability of 5 L/dm$^2$/min at a constant pressure of 3 bar to obtain a liquid and a solid phase. The liquid phase was then deionized by electrodialysis using bipolar membranes (ED64004, PCCell) with a membrane stack composed of 10 bipolar membranes (PCCell), 10 anion exchange membranes (PC 200D, PCCell) and 9 cation exchange membranes (PC SK, PCCell). The electrodialysis was performed at 32° C. for a duration of 2 h and with pump rates of 50 L/h for the diluate and the concentrate. After 2 h, the conductivity decreased by 83%. Weighing of the electrodialysis membranes after the deionization showed that these membranes had a lower weight in comparison to membranes used with non-treated hydrolysate (produced according to the state of the art process). The fouling on the membranes used with treated hydrolysate was thus reduced in comparison to performing the electrodialysis with non-treated hydrolysate (state of the art).

Figure 7:
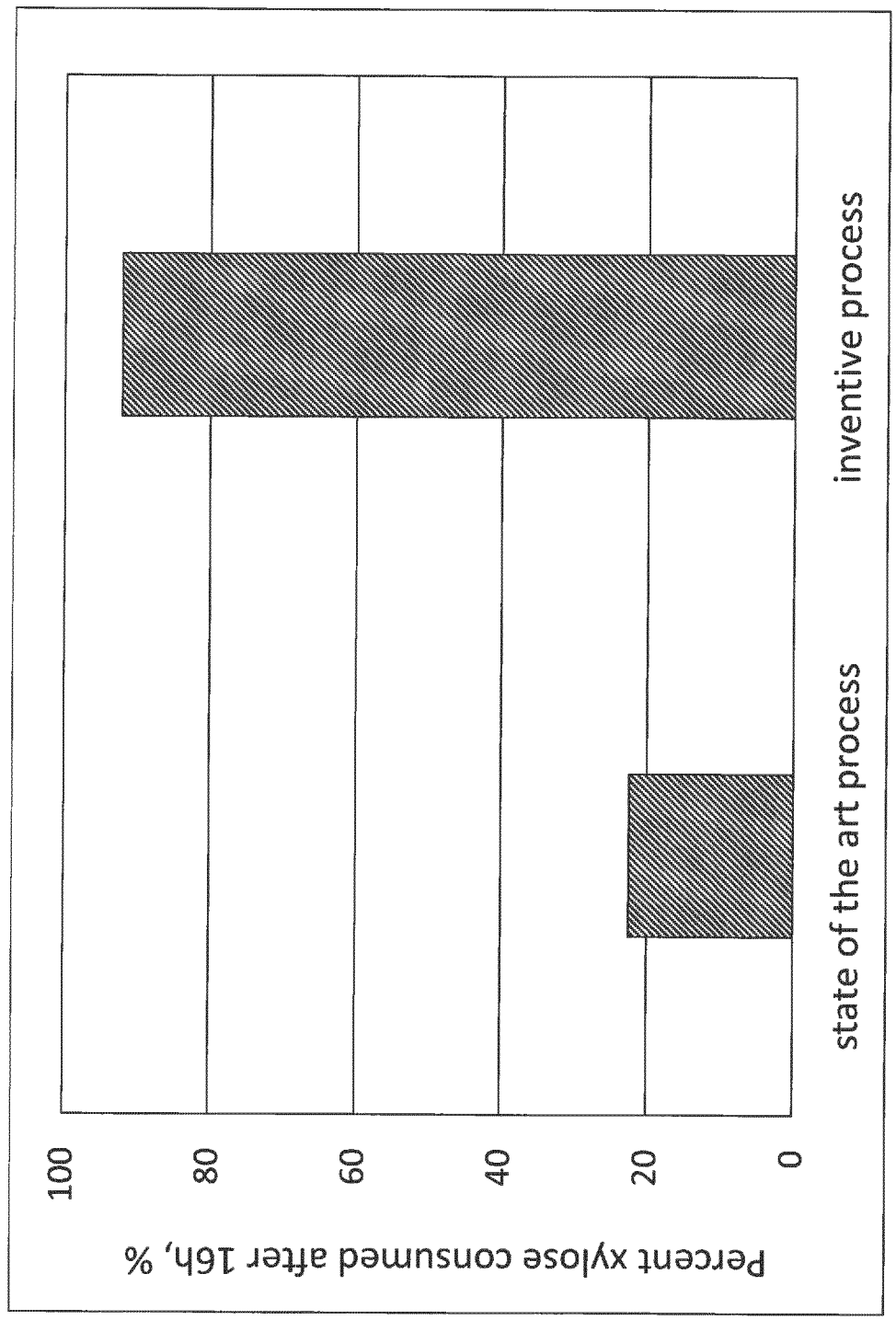
FIG. 7 shows the relative amount of xylose consumed after 16 h of fermentation of *Pachysolen tannophilus* when using hydrolysate treated according to the present invention as described in example 4.

After undergoing electrodialysis, the treated hydrolysate was used as substrate for the fermentation of *Pachysolen tannophilus*. The fermentation was performed in a stirred glass tank (Multifors, Infors AG, Switzerland) with a temperature and pH control device. The fermentation was started by adding 10% (wt./wt.) seed culture of *Pachysolen tannophilus* (DSMZ No. 70352, Braunschweig) to 750 mL of the treated hydrolysate after electrodialysis. The fermentation was performed in batch mode at 30° C. and pH 6.0, with stirring at 200 rpm for 100 hours. In comparison to non-treated hydrolysate, the xylose consumption rate was significantly increased when using the hydrolysate according to the inventive process, thus significantly accelerating the fermentation process, increasing the productivity and reducing costs. The results are shown in FIG. 7.

EXAMPLE 5

Cereal straw with a dry matter content of 45 wt.-% was pretreated by steam explosion (220° C.). After the steam explosion, the so pretreated cereal straw ("substrate") was introduced into a stirred tank (Labfors, Infors AG, Switzerland). An enzyme composition containing 91.3 wt.-% Celluclast® (Cellulase from *Trichoderma reesei* ATCC 26921, C2730 Sigma) and 8.7 wt.-% Glucosidase (49291 Sigma) was added to the substrate at an enzyme to solid ratio of 0.5 wt.-% to hydrolyze the substrate to obtain a slurry. The hydrolysis was carried out at 50° C., pH 5.0 for 72 hours with stirring at 50 rpm. After hydrolysis, the slurry was heated to 70° C. for 1 h while stirring at 200 rpm and then the pH was set to 2.5 using 1 M $H_2SO_4$. The so-treated slurry was then filtered using a filter press with filter cloth having a cloth air permeability of 5 L/dm²/min at a constant pressure of 3 bar to obtain a liquid and a solid phase. The liquid phase was then deionized by electrodialysis using bipolar membranes (ED64004, PCCell) with a membrane stack composed of 10 bipolar membranes (PCCell), 10 anion exchange membranes (PC 200D, PCCell) and 9 cation exchange membranes (PC SK, PCCell). The electrodialysis was performed at 32° C. for a duration of 2 h and with pump rates of 50 L/h for the diluate and the concentrate. After 2 h, the conductivity decreased by 83%. Weighing of the electrodialysis membranes after the deionization showed that these membranes had a lower weight in comparison to membranes used with non-treated hydrolysate (produced after state of the art process). The fouling on the membranes used with treated hydrolysate was thus reduced in comparison to performing the electrodialysis with non-treated hydrolysate (state of the art).

Figure 8:
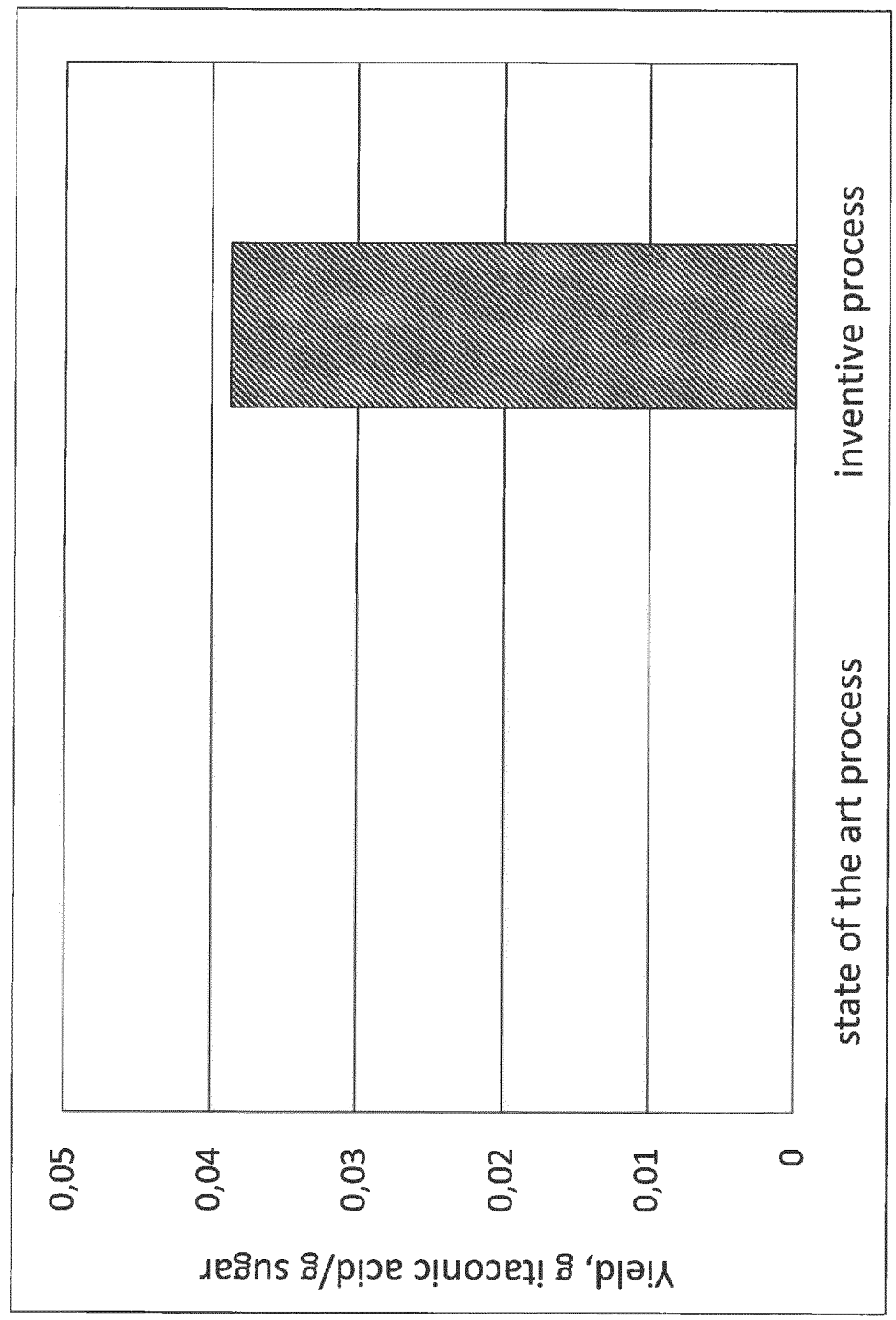
FIG. 8 shows the yield of the fermentation in terms of g itaconic acid produced after 100 h of fermentation of *Aspergillus terreus* per g sugar when using hydrolysate treated according to the present invention as described in example 5.

After undergoing electrodialysis, the treated hydrolysate was used as substrate for the fermentation of *Aspergillus terreus*. The fermentation was performed in 50 mL shake flasks placed in an incubator (Multitron, Infors AG, Switzerland). The fermentation was started by adding 10% (wt./wt.) seed culture of *Aspergillus terreus* (ATCC 32359) to 10 mL of the treated hydrolysate after electrodialysis. The fermentation was performed in batch mode at 35° C. and pH 3.0, with stirring at 250 rpm for 100 hours at 80% relative humidity. While the fermentation of *Aspergillus terreus* in non-treated hydrolysate did not show neither significant growth nor significant production of itaconic acid, the hydrolysate treated according to the present invention permitted significant cell growth and significant production of itaconic acid. The yield of the fermentation in terms of g itaconic acid per g sugar is shown in FIG. 8.

EXAMPLE 6

Cereal straw with a dry matter content of 45 wt.-% was pretreated by steam explosion (220° C.). After the steam explosion, the so pretreated cereal straw ("substrate") was introduced into a stirred tank (Labfors, Infors AG, Switzerland). An enzyme composition containing 91.3 wt.-% Celluclast® (Cellulase from *Trichoderma reesei* ATCC 26921, C2730 Sigma) and 8.7 wt.-% Glucosidase (49291 Sigma) was added to the substrate at an enzyme to solid ratio of 0.5 wt.-% to hydrolyze the substrate to obtain a slurry. The hydrolysis was carried out at 50° C., pH 5.0 for 72 hours with stirring at 50 rpm. After hydrolysis, the slurry was heated to 70° C. for 1 h while stirring at 200 rpm and then the pH was set to 2.5 using 1 M $H_2SO_4$. The so-treated slurry was then filtered using a filter press with filter cloth having a cloth air permeability of 5 L/dm²/min at a constant pressure of 3 bar to obtain a liquid and a solid phase. The liquid phase was then deionized by electrodialysis using bipolar membranes (ED64004, PCCell) with a membrane stack composed of 10 bipolar membranes (PCCell), 10 anion exchange membranes (PC 200D, PCCell) and 9 cation exchange membranes (PC SK, PCCell). The electrodialysis was performed at 32° C. for a duration of 2 h and with pump rates of 50 L/h for the diluate and the concentrate. After 2 h, the conductivity decreased by 83%. Weighing of the electrodialysis membranes after the deionization showed that these membranes had a lower weight in comparison to membranes used with non-treated hydrolysate (produced after state of the art process). The fouling on the membranes used with treated hydrolysate was thus reduced in comparison to performing the electrodialysis with non-treated hydrolysate (state of the art).

After undergoing electrodialysis, 200 mL of this treated hydrolysate was brought into contact with 30 g ion exchange resin (Lewatit® S6368 A, Lanxess) in a glass column XK16 using an Äkta Explorer (GE Healthcare) unit. The flow rate was 1 mL/min and the contacting was performed at 21° C.

Figure 9:
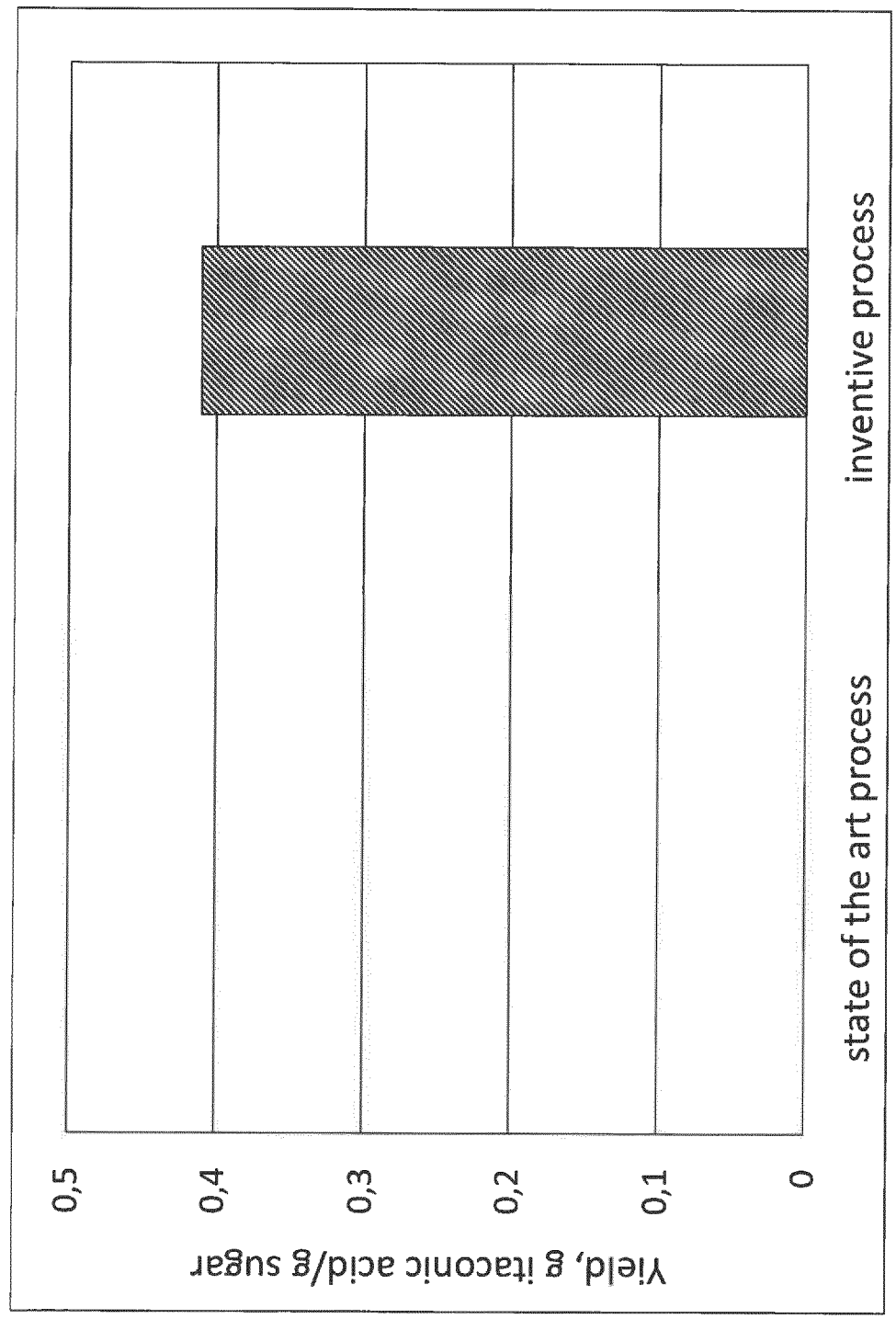
FIG. 9 shows the yield of the fermentation in terms of g itaconic acid produced after 100 h of fermentation of *Aspergillus terreus* per g sugar when using hydrolysate treated according to the present invention as described in example 6.

After undergoing electrodialysis and ion exchange chromatography, the treated hydrolysate was used as substrate for the fermentation of *Aspergillus ferrous*. The fermentation was performed in 50 mL shake flasks placed in an incubator (Multitron, Infors AG, Switzerland). The fermentation was started by adding 10% (wt./wt.) seed culture of *Aspergillus terreus* (ATCC 32359) to 10 mL of the treated hydrolysate after electrodialysis and ion exchange chromatography. The fermentation was performed in batch mode at 35° C. and pH 3.0, with stirring at 250 rpm for 100 hours at 80% relative humidity. While the fermentation of *Aspergillus terreus* in non-treated hydrolysate did not show neither significant growth nor significant production of itaconic acid, the hydrolysate treated according to the present invention permitted significant cell growth and significantly improved production of itaconic acid. The yield of the fermentation in terms of g itaconic acid per g sugar is shown in FIG. 9.

The invention claimed is:

1. Process for the purification of biomass hydrolysate comprising the steps
   a) Providing a biomass hydrolysate, wherein the hydrolysate is prepared by adding at least one hydrolase enzyme to the biomass;
   b) Adjusting the temperature of the biomass hydrolysate to a temperature selected from the range of from 50 to 95° C.;
   c) Addition of at least one acid to the biomass hydrolysate;
   d) Solid-liquid separation of the biomass hydrolysate-acid mixture to obtain a solid phase and a liquid phase;
   e) Deionization of the liquid phase of the biomass hydrolysate-acid mixture after separation according to step d).

2. Process according to claim 1, wherein the temperature according to step b) is selected from the range of from 65 to 90° C.

3. Process according to claim 1, wherein the at least one acid is added until a pH of from 2.0 to 4.5 of the biomass hydrolysate is reached.

4. Process according to claim 1, wherein the at least one acid has a pKa value of from −4.0 to 5.0.

5. Process according to claim 1, wherein at least one adsorbent is added before or during any of steps b) or d).

6. Process according to claim 5, wherein the at least one adsorbent is selected from the group consisting of bentonite, charcoal, activated carbon, diatomite, kieselguhr, bleaching earth, clay minerals, polymeric resins and any mixture thereof.

7. Process according to claim 1, wherein steps b) and c) are at least partially carried out concurrently.

8. Process according to claim 7, wherein the at least one acid is added during the adjustment of the temperature of the hydrolysate to a temperature selected from the range of from 65 to 90° C. from a temperature of 50° C. onwards.

9. Process according to claim 1, wherein the temperature of the at least one acid is selected from 5 to 45° C. and the at least one acid is added to the biomass hydrolysate at a temperature of the hydrolysate selected from the range of from 70 to 95° C.

10. Process according to claim 9, wherein the temperature difference between the at least one acid and the biomass hydrolysate is selected from the range of from 35 to 95%.

11. Process according to claim 1, wherein the deionization is carried out by electrodialysis, ion exchange chromatography, membrane capacitive deionization, nanofiltration, reverse osmosis, chromatographic separation, hydrophobic chromatography, size exclusion chromatography or any combination thereof.

12. Process according to claim 11, wherein deionization is carried out by electrodialysis followed by membrane capacitive deionization or by ion exchange chromatography.

13. Process according to claim 11, wherein deionization is carried out by electrodialysis using at least one bipolar membrane.

14. Process according to claim 11, wherein step c) is carried out before step b).

15. Process according to claim 1, wherein step c) is carried out before step b).

* * * * *